United States Patent
Hirota et al.

(10) Patent No.: US 6,814,937 B1
(45) Date of Patent: Nov. 9, 2004

(54) DISPENSER AND METHOD FOR PRODUCING DNA CHIP

(75) Inventors: Toshikazu Hirota, Owariasashi (JP); Takao Ohnishi, Nishikasugai-Gun (JP); Yukihisa Takeuchi, Nishikamo-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 218 days.

(21) Appl. No.: 09/694,130

(22) Filed: Oct. 23, 2000

(30) Foreign Application Priority Data

Oct. 22, 1999 (JP) .......................................... 11-301627
Mar. 23, 2000 (JP) ....................................... 2000-083020

(51) Int. Cl.$^7$ ................................................. B01L 3/02
(52) U.S. Cl. ............................. 422/100; 347/8; 347/20; 347/86; 73/863.32; 73/864.01
(58) Field of Search .............................. 422/100; 347/8, 347/20, 86; 73/863.32, 864.01

(56) References Cited

U.S. PATENT DOCUMENTS

| | | | | |
|---|---|---|---|---|
| 3,930,260 A | * | 12/1975 | Sicking ........................ 347/68 |
| 4,730,197 A | * | 3/1988 | Raman et al. ................. 347/40 |
| 5,223,225 A | * | 6/1993 | Gautsch ....................... 422/100 |
| 5,409,138 A | * | 4/1995 | Nakano ........................ 222/64 |
| 5,790,158 A | * | 8/1998 | Shinada et al. ............... 347/86 |
| 5,817,522 A | * | 10/1998 | Goodman et al. ........... 436/165 |
| 5,874,048 A | * | 2/1999 | Seto et al. .................. 422/100 |
| 5,874,971 A | * | 2/1999 | Nishioka et al. .............. 347/20 |
| 5,877,580 A | | 3/1999 | Swierkowski |
| 5,948,695 A | * | 9/1999 | Douglas et al. .............. 436/518 |
| 6,019,465 A | * | 2/2000 | Shinada et al. ................ 347/93 |
| 6,042,219 A | * | 3/2000 | Higashino et al. ............. 347/47 |
| 6,063,339 A | * | 5/2000 | Tisone et al. ................. 422/67 |
| 6,086,193 A | * | 7/2000 | Shimada et al. .............. 347/86 |
| 6,106,685 A | * | 8/2000 | McBride et al. ............. 204/600 |
| 6,123,905 A | * | 9/2000 | Torti et al. ................... 422/100 |
| 6,251,343 B1 | * | 6/2001 | Dubrow et al. ............. 422/102 |
| 6,280,148 B1 | | 8/2001 | Zengerle et al. |
| 6,312,115 B1 | * | 11/2001 | Hara et al. ..................... 347/86 |
| 6,368,562 B1 | * | 4/2002 | Yao ............................ 422/100 |
| 6,461,812 B2 | * | 10/2002 | Barth et al. .................... 435/6 |

FOREIGN PATENT DOCUMENTS

| | | | |
|---|---|---|---|
| JP | 57-115351 A | * | 7/1982 |
| JP | 04-327943 A | * | 11/1992 |
| JP | 6-040030 A | | 2/1994 |
| WO | 98/36832 | | 8/1988 |

* cited by examiner

Primary Examiner—Arlen Soderquist
Assistant Examiner—Elizabeth Quan
(74) Attorney, Agent, or Firm—Burr & Brown

(57) ABSTRACT

A dispenser includes a plurality of arranged micropipettes, each including a sample-pouring port for pouring a sample solution from the outside, a cavity for pouring and charging the sample solution thereinto, and a sample discharge port for discharging the sample solution, and formed on at least one or more substrates. The micropipette further includes an actuator section disposed on at least one wall surface of the substrate which forms the cavity so that the sample solution is movable in the cavity, and the sample solution is discharged from the sample discharge port of each of the micropipettes. A pin, which protrudes upwardly, is provided at the sample-pouring port of each of the micropipettes.

9 Claims, 22 Drawing Sheets

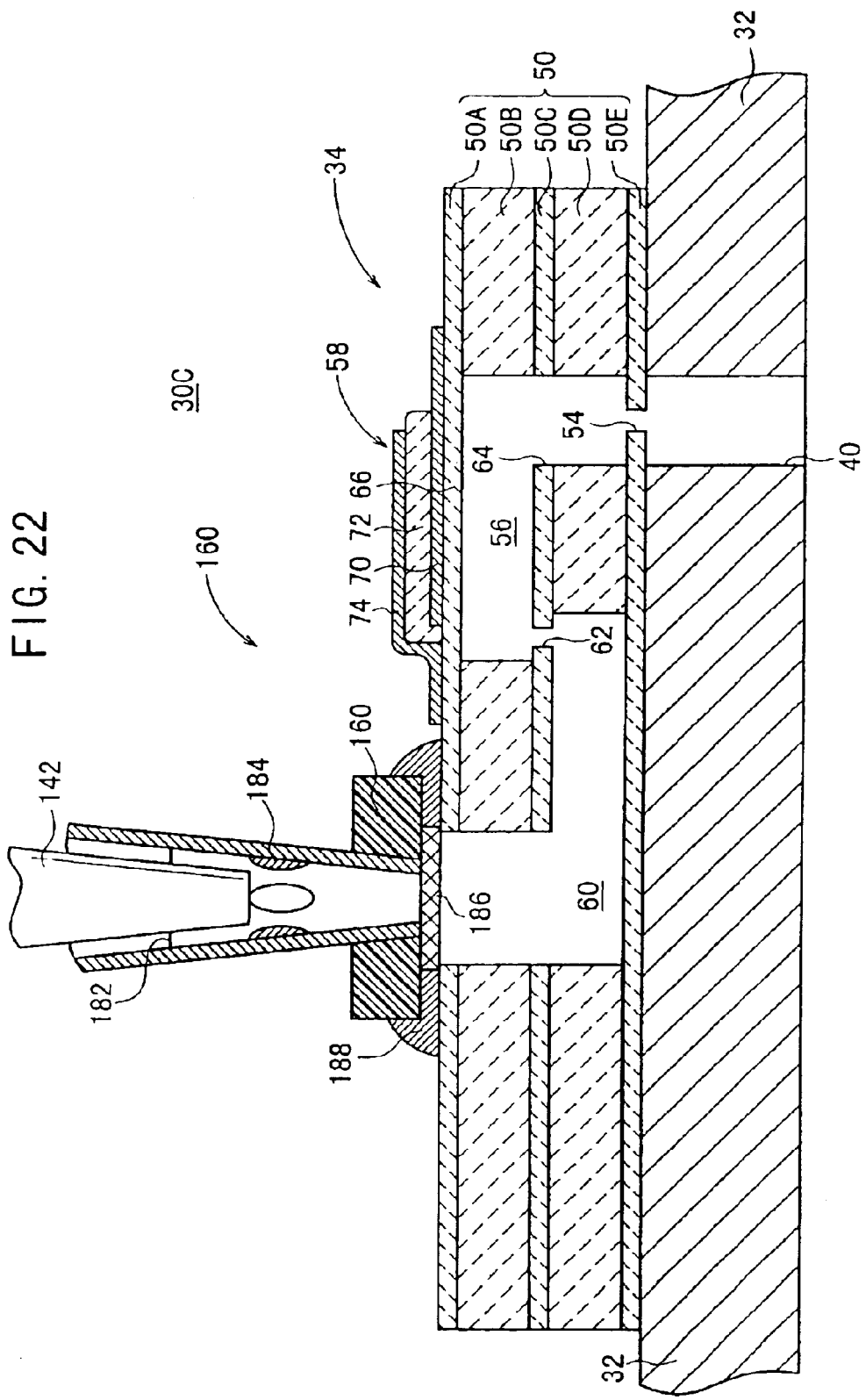

DISPENSER AND METHOD FOR PRODUCING DNA CHIP

BACKGROUND OF THE INVENTION

1. Field of the Invention

The present invention relates to a dispenser to be used for the production of a DNA chip (DNA microarray) in which several thousands to not less than ten thousands kinds of different types of DNA fragments are aligned and fixed as minute spots at a high density on a base plate such as a microscopic glass slide, and a method for producing a DNA chip by using the dispenser.

2. Description of the Related Art

The method for analyzing the genetic structure has been remarkably progressed in recent years. A large number of genetic structures represented by those of the human genome have been clarified. The analysis of the genetic structure as described above uses a DNA chip (DNA microarray) in which several thousands to not less than ten thousands kinds of different types of DNA fragments are aligned and fixed as spots on a base plate such as a microscopic glass slide.

Those widely used as a method for forming the spots for the production of the DNA chip are based on a system such as the QUILL system, the pin & ring system, and the spring pin system in which a sample solution containing DNA fragments is supplied (stamped) onto the base plate by using a so-called pin. Even when any one of the foregoing methods is adopted, it is necessary to suppress the dispersion of the volume and the shape of each of the spots to be low so that the distance between the respective spots is maintained to be constant.

On the other hand, in order to realize a higher density, it is also greatly expected to develop a new method which is excellent in productivity and in which the shape control performance for the spot is satisfactory.

The QUILL system lies in a method in which a sample is stored in a recess formed at a pin tip, and the pin tip is allowed to make contact with the base plate so that the sample in the recess is transferred onto the base plate to form a minute spot. However, this system involves, for example, a problem of durability such that the pin tip is deformed or it is damaged by the contact with the base plate. Further, this system also involves, for example, a problem such that the sample stored in the recess is incompletely washed to facilitate the occurrence of cross-contamination.

The pin & ring system lies in a method in which a sample solution in a microplate is reserved with a ring, and then the sample in the ring is trapped by a pin tip so that the pin tip penetrates through the inside of the ring reserved with the solution to form a spot on the base plate. However, the sample, which can be reserved once, depends on the number of rings. Conventionally, the number of rings can not be increased. For this reason, in order to form several thousands to several tens of thousands of minute sample spots, it is also necessary to perform washing and drying steps several hundreds to several thousands of times. Therefore, it is difficult to say that the productivity is necessarily high.

The spring pin system lies in a method in which a sample adhered to a pin tip is transferred onto the base plate by pressing the pin tip against the base plate. A double pin structure containing a spring is used to mitigate the damage of the pin and the base plate while the sample is ejected. However, basically, only one time of spotting can be performed with one time of reserve. This system is inferior in productivity.

In all of the conventional methods for forming the minute spots, the sample solution is transported onto the base plate in a state of being exposed to the atmospheric air. Therefore, an inconvenience arises such that the sample is dried during the transport, and it is impossible to perform the spotting. A problem arises such that the extremely expensive sample solution is used with bad efficiency.

On the other hand, a method is also investigated by using the so-called ink-jet system which is practically used for printers. However, many tasks arise concerning the size and the cost when several thousands to several tens of thousands of individual flow passages corresponding to every sample are formed. Further, in the case of the ink-jet system, it is necessary to previously charge the sample in a pump before the spotting so that no bubble is formed. For this reason, a large amount of sample is required to effect the purge. Therefore, the efficiency of the use of the sample is extremely inferior. In general, in order to remove the bubble, it is preferable to move the liquid at a high speed in the flow passage including a pump chamber. As a result, the sample is agitated in the flow passage. When a delicate DNA solution is used as a sample, for example, DNA is damaged in some cases.

SUMMARY OF THE INVENTION

The present invention has been made taking the foregoing problems into consideration, an object of which is to provide a dispenser which comprises a large number of micropipettes arranged to makes it possible to form minute spots accurately at a high speed, which makes it possible to supply a solution to the respective micropipettes quickly and reliably, and which makes it possible to smoothly perform the steps from the supply of the solution to the supply onto a base plate.

Another object of the present invention is to provide a method for producing a DNA chip, which makes it possible to smoothly perform the steps from the supply of a solution to the supply onto a base plate and which makes it possible to improve the quality of the DNA chip and improve the yield.

According to the present invention, there is provided a dispenser comprising a plurality of arranged micropipettes each including a pouring port for pouring a sample solution from the outside, a cavity for pouring and charging the sample solution thereinto, and a discharge port for discharging the sample solution, formed on at least one or more substrates. The micropipette further includes a piezoelectric/electrostrictive element disposed on at least one wall surface of the substrate which forms the cavity so that the sample solution is movable in the cavity, and the sample solution is discharged from the discharge port of each of the micropipettes; wherein a pin, which protrudes upwardly, is provided at the pouring port of each of the micropipettes.

According to another aspect of the present invention, there is provided a method for producing a DNA chip, comprising the steps of using a dispenser comprising a plurality of arranged micropipettes each including a pouring port for pouring a sample solution from the outside, a cavity for pouring and charging the sample solution thereinto, and a discharge port for discharging the sample solution, formed on at least one or more substrates. The micropipette further includes a piezoelectric/electrostrictive element disposed on at least one wall surface of the substrate which forms the cavity so that the sample solution is movable in the cavity; and discharging the sample solution onto a base plate from the discharge port of each of the micropipettes to produce the DNA chip; wherein the dispenser to be used is provided with a pin protruding upwardly at the pouring port of each of the micropipettes.

Accordingly, a hole can be bored with the pin through a solution storage section of a cartridge positioned over the pouring port so that the solution stored in the solution storage section may be introduced into the pouring port.

That is, a cartridge, which is arranged with a large number of solution storage sections, is positioned over the dispenser, and the cartridge is moved toward the dispenser. At this time, a hole is bored with the pin through each of the solution storage sections. Accordingly, the solution stored in the solution storage section is introduced into the pouring port along the pin. By doing so, it is unnecessary to use any special apparatus when the sample solution is poured into the dispenser from the solution storage section of the cartridge. Thus, no sample solution remains in the special apparatus, and the efficiency of the use of the sample solution is not lowered.

In this process, it is also preferable that when the solution stored in the solution storage section is introduced into the pouring port, a gas is fed under pressure downwardly to each of the solution storage sections. Accordingly, it is possible to shorten the period of time required to pour the solution.

In the present invention, the solution stored in the solution storage section can be introduced into the pouring port by boring a hole through a film member coated to close the solution storage section of the cartridge positioned over the pouring port.

That is, a cartridge, which is arranged with a large number of solution storage sections, is coated with a film member to close the solution storage sections; the cartridge is positioned over the dispenser so that the film member is opposed to the dispenser; and the cartridge is moved toward the dispenser. During this process, a hole is bored with the pin through a portion of the film member corresponding to each of the solution storage sections. Accordingly, the solution stored in the solution storage section is introduced into the pouring port along the pin.

It is possible to carry out the process to bore the hole through the film member relatively conveniently, as compared with the process to bore the hole through the solution storage section of the cartridge. Therefore, it is easy to introduce the sample solution.

As described above, the dispenser according to the present invention can be used to supply the solution to the respective micropipettes quickly and reliably. It is possible to perform the steps from the supply of the solution to the supply onto the base plate.

The pin described above refers to a projection-shaped section having a portion protruding from the plane. It is preferable that the forward end is sharp. It is preferable that the arrangement position of each of the pouring ports of the micropipettes for constructing the dispenser is equal to the arrangement position of each of the solution storage sections of the cartridge provided with the solution storage sections. Alternatively, it is preferable that the arrangement pitch is an integral multiple of the arrangement pitch of the solution storage sections, or an integral fraction thereof.

The pin may be provided at a position included in the pouring port as viewed in plan view, or it may be provided at a circumferential edge of the pouring port. When the pin is provided at the position included in the pouring port as viewed in plan view, the hole, through which the sample solution is introduced, can be positioned just over the pouring port. Thus, it is possible to introduce the sample solution more reliably. When the pin is provided at the circumference of the pouring port, then it is easy to form the pin, and the production cost of the dispenser is reduced.

In the present invention, it is also preferable that a holding section for holding a pipette for pouring the solution from the pouring port or a tube for receiving the pipette is provided at a circumferential edge of the pouring port of each of the micropipettes for constructing the dispenser.

Accordingly, when the solution is poured into each of the micropipettes of the dispenser by using the pipette, the pipette or the tube for receiving the pipette is held by the holding section. Therefore, it is possible to pour the solution into the micropipette in a reliable manner. It is possible to effectively avoid, for example, any leakage of the solution.

Especially, at least the inner wall of the tube for receiving the pipette is subjected to a hydrophilic treatment. Thus, the solution, which is discharged from the pipette, can be reliably introduced into the pouring port of the micropipette without involving any bubble or the like.

In the present invention, it is also preferable that a scale for measuring an amount of liquid poured into the tube is formed at least at a part of the tube for receiving the pipette. It is also preferable that a portion provided with a projection and a portion provided with no projection are formed at positions of an identical distance from the pouring port on a part of an inner wall of the tube for receiving the pipette.

When the scale is formed, it is possible to measure and confirm the amount of the poured sample solution while pouring the sample solution, and the amount of the discharged sample solution while discharging the sample solution. Thus, the scale is useful to manage the production of the product and manage the quality. Further, the scale is effective to manage the liquid amount of a substitution solution or an intermediate solution in the case of the use of a method in which the substitution solution or the intermediate solution is previously charged, when the sample solution is poured and charged into the micropipette. As a result, it is possible to perform the substitution of the substitution solution certainly or the intermediate solution with the sample solution. Thus, it is possible to reduce the dispersion of the concentration of the sample solution to be supplied, and the quality of the product is improved.

When the portion provided with the projection and the portion provided with no projection are formed at the positions of the identical distance from the pouring port on the part of the inner wall of the tube for receiving the pipette, it is possible to perform the introducing operation while allowing the forward end of the pipette for introducing the sample solution to make contact with the projection. The injection position of the pipette can be always made to be constant, and the dispersion of the introducing operation is reduced.

The presence of the portion provided with the projection and the portion provided with no projection ensures the escape route for the gas during the pouring process. It is possible to perform the introducing operation without involving any bubble or the like. It is noted that such an effect is exhibited not only when the sample solution, the substitution solution or the like is introduced (poured). The foregoing arrangement is also effective when the pipetting is performed in order to remove an excessive amount of the sample solution, the substitution solution, or the intermediate solution.

In the present invention, it is preferable that a filter, which is formed with a large number of openings having an opening area of not more than an opening area of the discharge port, is attached between the pouring port and the tube for receiving the pipette, in order to remove any foreign matter in the sample solution to be poured. By doing so, it is possible to previously avoid the invasion of the foreign matter into the micropipette, the clogging of the discharge port or the like, and the failure of the supply of the sample solution.

In the present invention, it is also preferable that the dispenser further comprises a pitch-varying mechanism for varying an arrangement pitch of each of the micropipettes for constructing the dispenser.

Accordingly, the solution can be supplied to the dispenser while allowing the arrangement pitch of the respective micropipettes of the dispenser to conform to an arrangement pitch of respective pipettes of a solution supply means for supplying the solution to the dispenser; and the sample solution can be supplied from the dispenser onto the base plate while setting the arrangement pitch of the respective micropipettes of the dispenser to be a pitch which is different from the arrangement pitch of the respective pipettes of the solution supply means. It is possible to perform the steps from the supply of the solution to the supply onto the base plate continuously.

That is, in general, the supply (pouring or introduction) of the sample solution to the micropipette and the dispenser is often restricted by the size of the solution supply means or the cartridge having the solution storage section. It is inevitable to give a relatively large arrangement pitch for the respective pipettes or the pouring ports of the respective micropipette. On the other hand, when the sample solution is supplied onto the base plate, the small supply pitch is advantageous in many cases in view of the spot density and the number of spots capable of being supplied once. In such a situation, the dispenser according to the present invention is preferably adopted.

In the present invention, it is also preferable that a solution supply means, which is arranged with a large number of pipettes for supplying the solution to the dispenser and which has a pitch-varying mechanism for varying an arrangement pitch of the respective pipettes, is used; the solution is supplied to the solution supply means while allowing the arrangement pitch of the respective pipettes to conform to an arrangement pitch of solution storage sections of a cartridge; and the solution is supplied from the solution supply means to the dispenser while allowing the arrangement pitch of the respective pipettes to conform to an arrangement pitch of the micropipettes of the dispenser.

In this case, it is possible to smoothly perform the process for supplying, to the dispenser, the solution stored in the respective solution storage sections of the cartridge. It is possible to effectively shorten the period of time required for the production.

In the present invention, when the dispenser is used, it is also preferable to adopt the following procedure. That is, no pin is provided for the dispenser. A cartridge, which is arranged with a large number of solution storage sections, is positioned over the dispenser. A pin is externally used to bore a hole through each of the solution storage sections so that the solution stored in the solution storage section is introduced into the pouring port. In this case, a simple structure can be used for each of the micropipettes of the dispenser.

When the hydrophilic treatment is applied to the pouring port of the dispenser described above, the sample solution, which is supplied via the pouring port, can be smoothly introduced toward the cavity. Therefore, it is possible to shorten the period of time required to supply the sample solution.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 22 shows a sectional view illustrating an arrangement of still another example of the micropipette of the dispenser according to the third embodiment.

DETAILED DESCRIPTION OF THE INVENTION

Exemplary embodiments of the dispenser and the method for producing the DNA chip according to the present invention will be explained below with reference to FIGS. 1 to 22.

Figure 1:
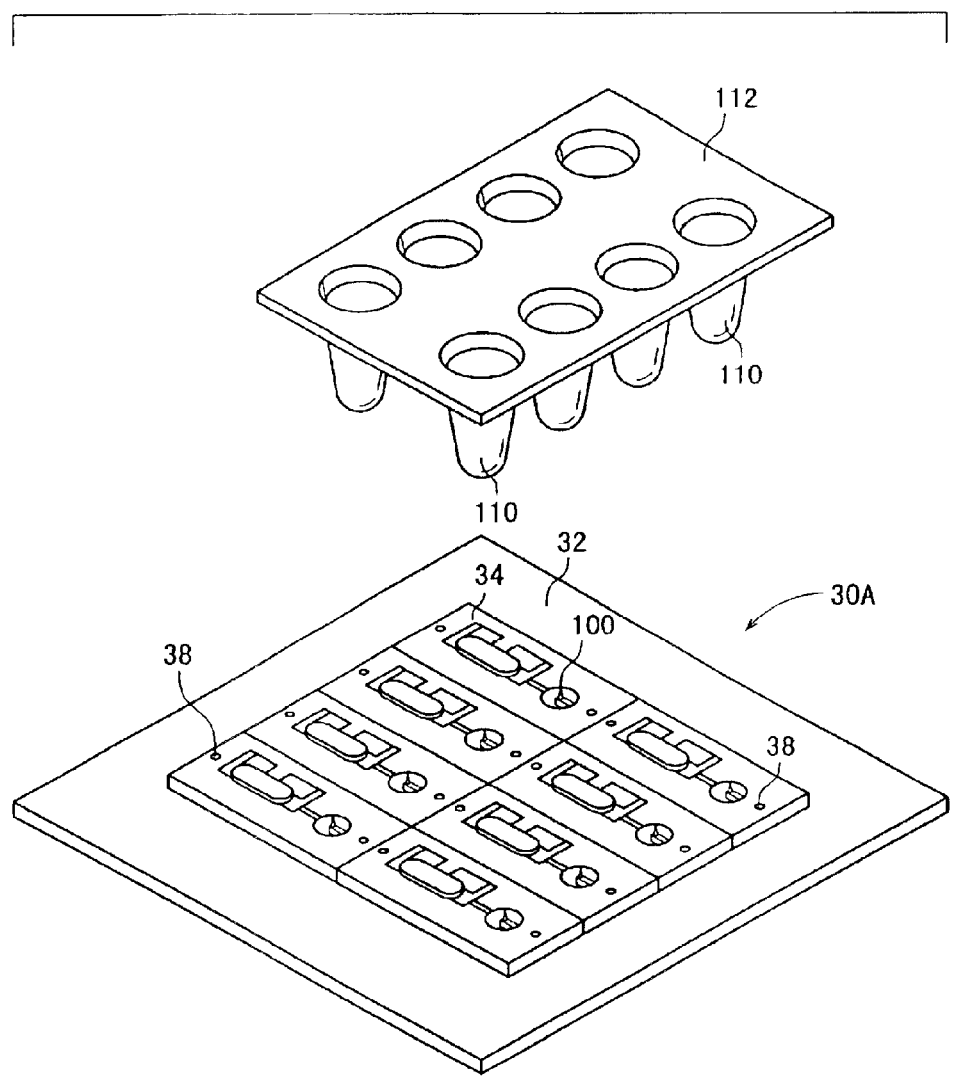
FIG. 1 shows a perspective view depicting an arrangement of a dispenser according to a first embodiment together with a cartridge, in order to illustrate a first method for producing a DNA chip by using the dispenser.

At first, as shown in FIG. 1, a dispenser 30A according to a first embodiment comprises a plurality of micropipettes 34 which are arranged in a matrix form on an upper surface of a rectangular fixation plate 32. The embodiment shown in FIG. 1 is illustrative of a case in which ten micropipettes 34 are arranged in five rows and two columns.

Figure 2:
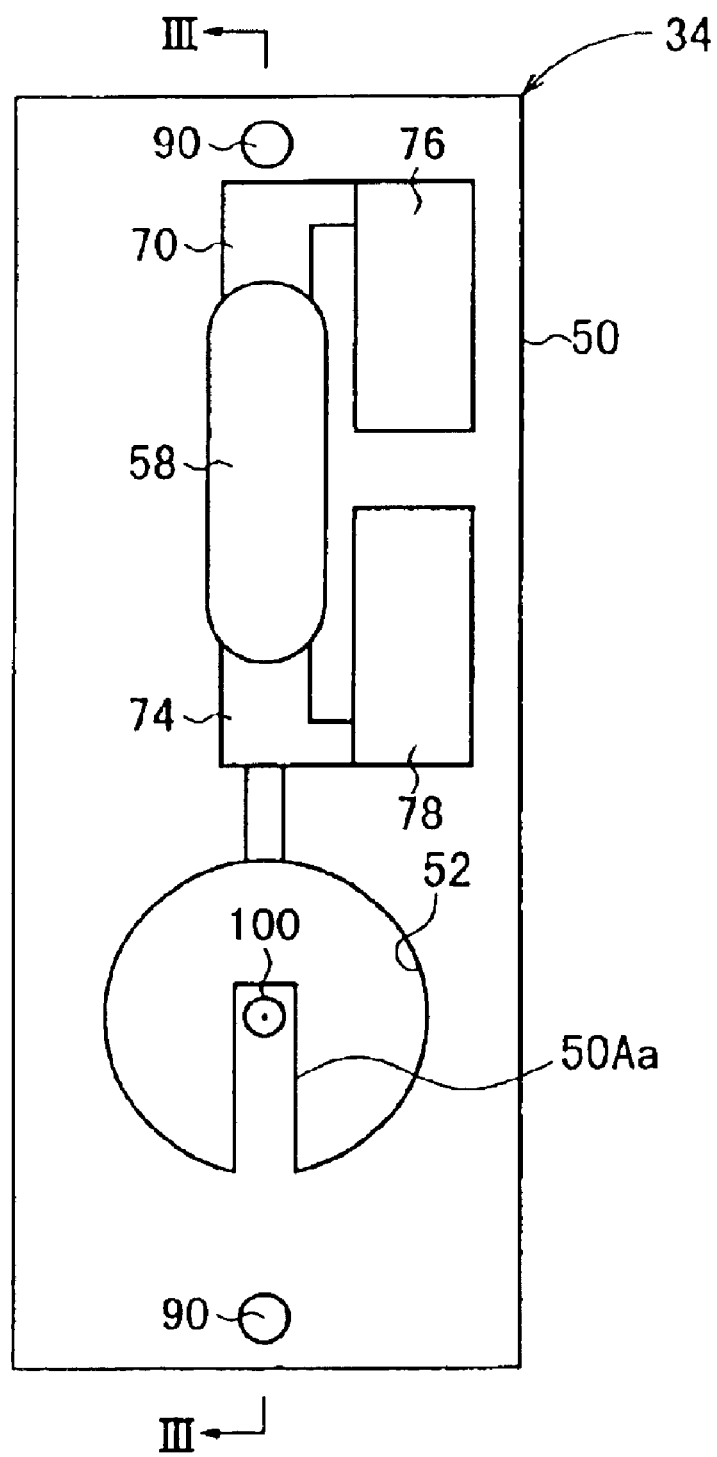
FIG. 2 shows a plan view illustrating a micropipette which constitutes the dispenser according to the first embodiment.
Figure 3:
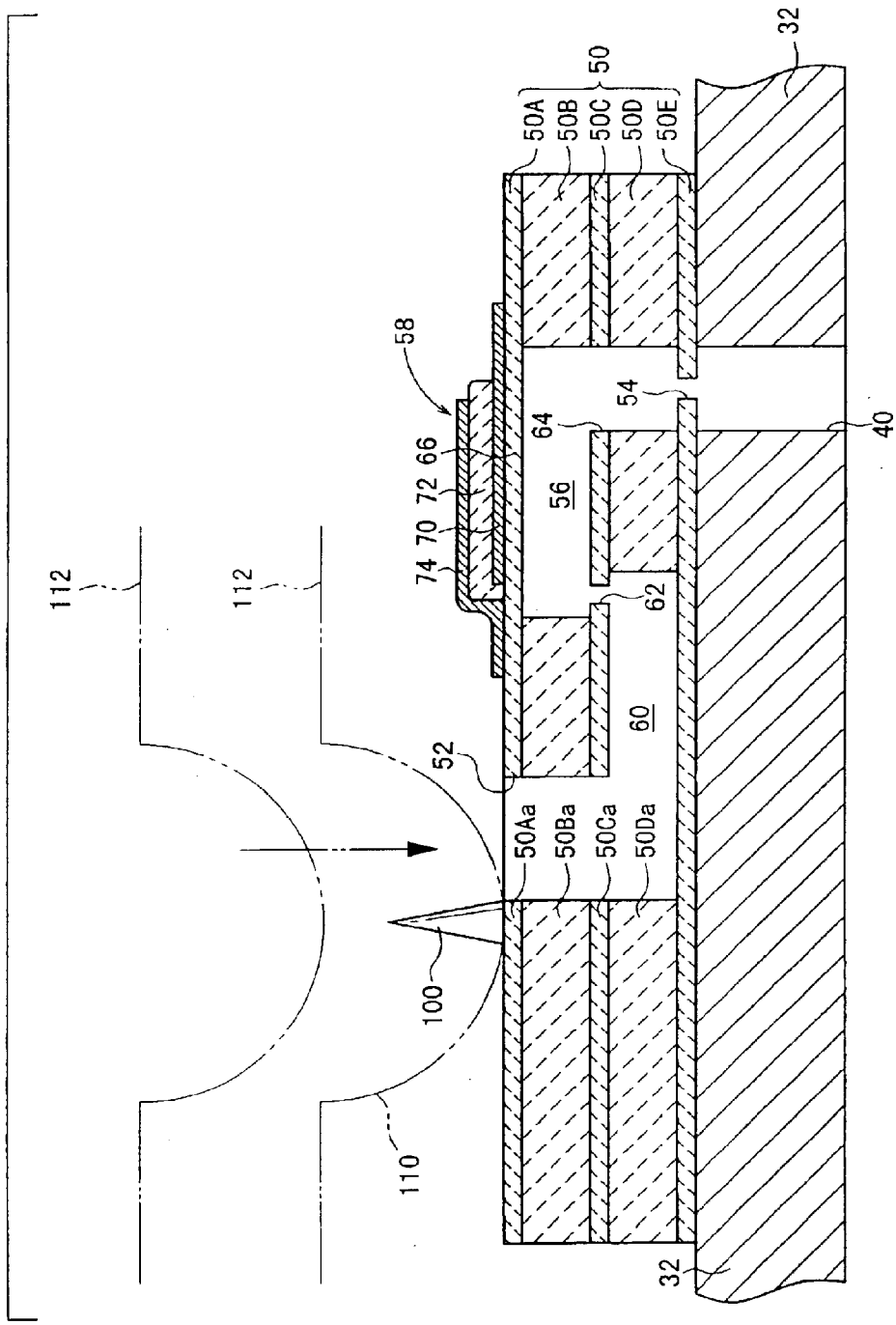
FIG. 3 shows a sectional view taken along a line III—III shown in FIG. 2.

As shown in FIGS. 2 and 3, the micropipette 34 comprises a sample-pouring port 52 which is formed at the upper surface of a substrate 50 having a substantially rectangular parallelepiped-shaped configuration, a sample discharge port 54 which is formed at the lower surface of the substrate 50, a cavity 56 which is formed at the inside between the sample-pouring port 52 and the sample discharge port 54, and an actuator section 58 which is used to vibrate the substrate 50 (correctly a vibrating section 66 as described later on) or change the volume of the cavity 56.

Therefore, as shown in FIG. 3, through-holes 40 are provided through the fixation plate 32 at portions corresponding to the sample discharge ports 54 of the micropipettes 34 respectively. Accordingly, a sample solution, which is discharged from the sample discharge port 54 of the micropipette 34, is supplied (or dropped) through the through-hole 40, for example, to a base plate 20 which is fixed under the fixation plate 32.

An introducing bore 60 having a substantially L-shaped configuration with a large opening is formed over a region ranging from the sample-pouring port 52 to the inside of the substrate 50 in the micropipette 34. A first communication hole 62 having a small diameter is formed between the introducing bore 60 and the cavity 56. The sample solution, which is poured from the sample-pouring port 52, is introduced into the cavity 56 through the introducing bore 60 and the first communication hole 62.

A second communication hole 64, which communicates with the sample discharge port 54 and which has a diameter larger than that of the first communication hole 62, is formed at a position different from that of the first communication hole 62, of the cavity 56. In the first embodiment, the first communication hole 62 is formed at the lower surface of the cavity 56. The position of the first communication hole 62 is deviated toward the sample-pouring port 52. The second communication hole 64 is formed at the position of the lower surface of the cavity 56 as well corresponding to the sample discharge port 54.

Further, in the first embodiment, the portion of the substrate 50, which is the upper surface of the cavity 56, is thin-walled to give a structure which tends to undergo the vibration with respect to the external stress so that the portion functions as a vibrating section 66. The actuator section 58 is formed on the upper surface of the vibrating section 66.

The substrate 50 is constructed by laminating a plurality of green sheets made of zirconia ceramics (first thin plate layer 50A, first spacer layer 50B, second thin plate layer 50C, second spacer layer 50D, and third thin plate layer 50E) followed by sintering into one unit.

That is, the substrate 50 is constructed by laminating the thin-walled first thin plate layer 50A which is formed with a window for constructing the sample-pouring port 52 and which constitutes a part of the vibrating section 66, the thick-walled first spacer layer 50B which is formed with a part of the introducing bore 60 and a plurality of windows for constructing the cavity 56 respectively, the thin-walled second thin plate layer 50C which is formed with a part of the introducing bore 60 and a plurality of windows for constructing a part of the second communication hole 64 and the first communication hole 62 respectively, the thick-walled second spacer layer 50D which is formed with a plurality of windows for constructing a part of the introducing bore 60 and a part of the second communication hole 64 respectively, and the thin-walled third thin plate layer 50E which is formed with a window for constructing the sample discharge port 54, followed by sintering into one unit.

The actuator section 58 is constructed to have the vibrating section 66 described above as well as a lower electrode 70 which is directly formed on the vibrating section 66, a piezoelectric layer 72 which is composed of, for example, a piezoelectric/electrostrictive element or an anti-ferroelectrics formed on the lower electrode 70, and an upper electrode 74 which is formed on the upper surface of the piezoelectric layer 72.

As shown in FIG. 2, the lower electrode 70 and the upper electrode 74 are electrically connected to an unillustrated driving circuit via a plurality of pads 76, 78 which are formed on the upper surface of the substrate 50 respectively.

The micropipette 34 constructed as described above is operated as follows. That is, when an electric field is generated between the upper electrode 74 and the lower electrode 70, then the piezoelectric layer 72 is deformed, and the vibrating section 66 is deformed in accordance therewith. Accordingly, the volume of the cavity (pressurizing chamber) 56 contacting with the vibrating section 66 is decreased or increased.

Figure 6:
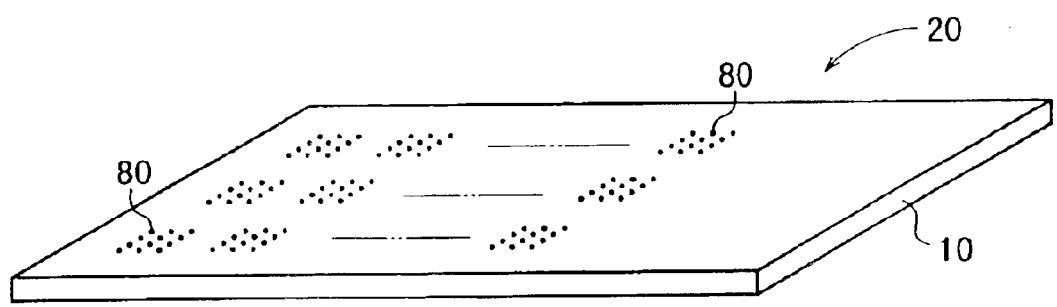
FIG. 6 shows a perspective view illustrating the DNA chip to be produced.

When the volume of the cavity 56 is decreased, the sample solution charged in the cavity 56 is discharged at a predetermined speed from the sample discharge port 54 which communicates with the cavity 56. As shown in FIG. 6, it is possible to prepare a DNA chip 20 in which the sample solutions discharged from the micropipettes 34 are aligned and fixed as minute spots 80 on a base plate 10 such as a microscopic slide glass. When the volume of the cavity 56 is increased, the sample solution is newly poured and charged from the communication hole 62 into the cavity 56 to make provision for the next discharge.

In this arrangement, the arrangement pitch of the sample discharge ports 54 in the dispenser 30A is larger than the arrangement pitch of the minute spots 80 formed on the base plate 10. Therefore, the sample solution is supplied while deviating the supply position for the dispenser 30A at every supplying time.

An apparatus structure based on the so-called ink-jet system (see Japanese Laid-Open Patent Publication No. 6-40030) may be adopted as the structure in which the volume of the cavity 56 is decreased in accordance with the driving of the actuator section 58.

The cavity (pressurizing chamber) 56 is formed to have such a flow passage dimension that the sample solution containing DNA fragments or the like is moved without any turbulence.

Figure 4:
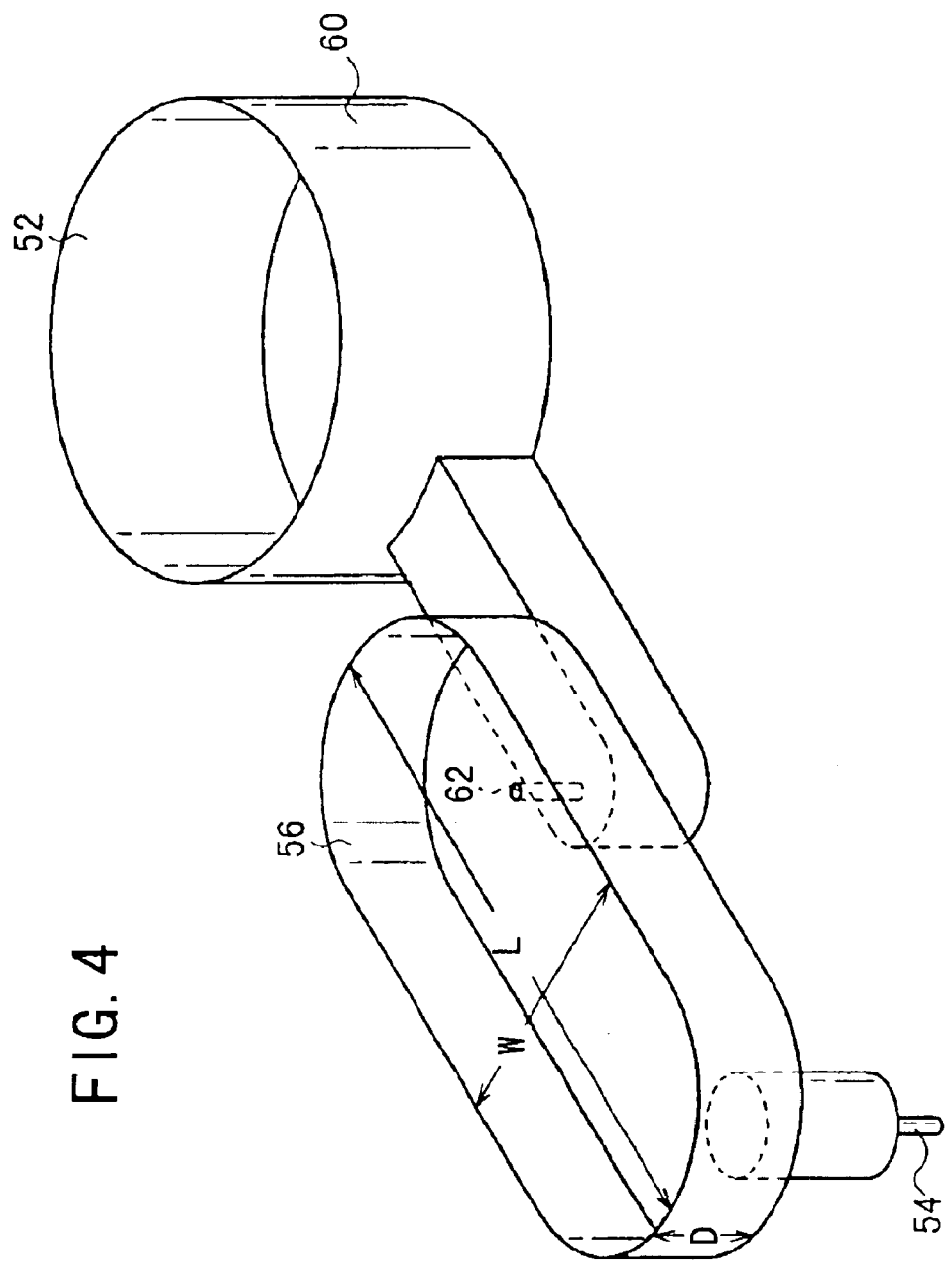
FIG. 4 shows a perspective view illustrating a shape of a flow passage including a cavity formed in a substrate of the micropipette.

That is, the dimension of the cavity 56 differs depending on the type of the sample, the size of liquid droplets to be prepared, and the density of, spotting formation. However, for example, when DNA fragments which length is about 1 to 10,000 base pairs are dissolved in a ×1 TE buffer solution at a concentration of not more than 100 $\mu g/\mu l$, and a sample, which is obtained by mixing with an aqueous solution containing an equivalent amount of polymer, is dripped at a pitch of 50 to 600 $\mu m$ to give a liquid droplet diameter of 30 to 500 $\mu m \phi$, then it is preferable that the cavity length (L) is 1 to 5 mm, the cavity width (W) is 0.1 to 1 mm, and the cavity depth (D) is 0.1 to 0.5 mm as shown in FIG. 4. It is preferable that the inner wall of the cavity 56 is smooth without involving any projection to disturb the flow. It is more preferable that the material of the cavity 56 is made of ceramics which has good affinity with respect to the sample solution.

When the shape as described above is adopted, the cavity 56 can be used as a part of the flow passage ranging from the sample-pouring port 52 to the sample discharge port 54. The sample can be introduced to the sample discharge port 54 without disturbing the flow of the sample solution which is moved from the sample-pouring port 52 via the introducing bore 60 and the first communication hole 62 to the inside of the cavity 56.

The substrate 50 is the sintered product obtained by laminating the zirconia ceramics into one unit as described above. Alternatively, the substrate 50 may be a bonded product composed of a sintered matter of zirconia ceramics formed with the actuator section 58, and a metal or resin film or the like. Especially, the thin plate layer 50E, in which the sample discharge port 54 is formed, is preferably a sheet obtained by processing an organic resin such as a PET film by means of an excimer laser or the like, or a sheet obtained by punching a metal such as a stainless steel film with a punch and die or the like, considering the matching with the processing method therefor.

The sizes of the sample discharge port 54 and the first communication hole 62 are optimally designed depending on, for example, the physical property, the discharge amount, and the discharge speed of the sample solution to be discharged. However, they are preferably about 10 to 100 $\mu m \phi$.

Figure 5:
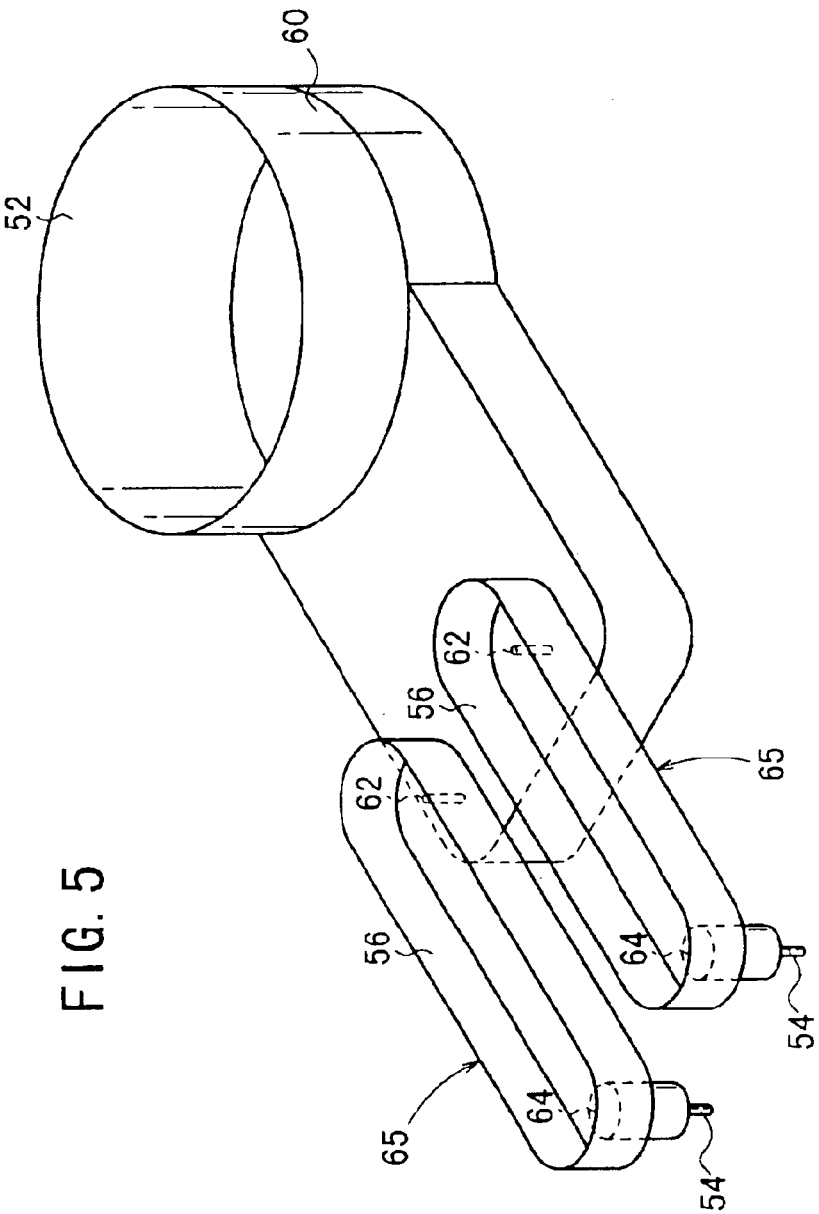
FIG. 5 shows a perspective view illustrating another shape of flow passages including cavities formed in a substrate of the micropipette.

In FIG. 5, two of the first communication holes 62 communicate with one sample-pouring port 52 and the introducing bore 60 connected thereto. Two flow passages 65, in each of which the cavity 56, the second communication hole 64, and the sample discharge port 54 are continuously formed, are independently formed for the first communication holes 62 respectively. Actuator sections 58 (not shown), which are wired and driven independently respectively, are formed on the upper surfaces of the respective cavities 56. When the micropipette 34 constructed as described above is used, it is possible to supply an identical sample solution onto the base plate 10 simultaneously or at any deviated timing.

As shown in FIG. 1, a plurality of pins 38 for positioning and fixing the micropipettes 34 are provided on the upper surface of the fixation plate 32. When the micropipette 34 is fixed on the fixation plate 32, the micropipette 34 is placed on the fixation plate 32 while inserting the pins 38 of the fixation plate 32 into positioning holes 90 (see FIG. 2) provided at the both sides in of the substrate 50 of the micropipette 34. Thus, a plurality of micropipettes 34 are automatically positioned with a predetermined array arrangement.

In the first embodiment, as shown in FIGS. 2 and 3, a pin 100 is provided to protrude upwardly from the sample-pouring port 52. The embodiment shown in FIGS. 2 and 3 is illustrative of the arrangement wherein protruding sections 50Aa, 50Ba, 50Ca, 50Da, which protrude, for example, toward the center of the sample-pouring port 52, are integrally provided for the four layers 50A to 50D except for the lowermost layer of the third thin plate layer 50E, of the respective layers 50A to 50E for constructing the substrate 50. The pin 100 is secured, for example, with an adhesive to the upper surface of the protruding section 50Aa of the upper layer (first thin plate layer 50A).

Figure 7:
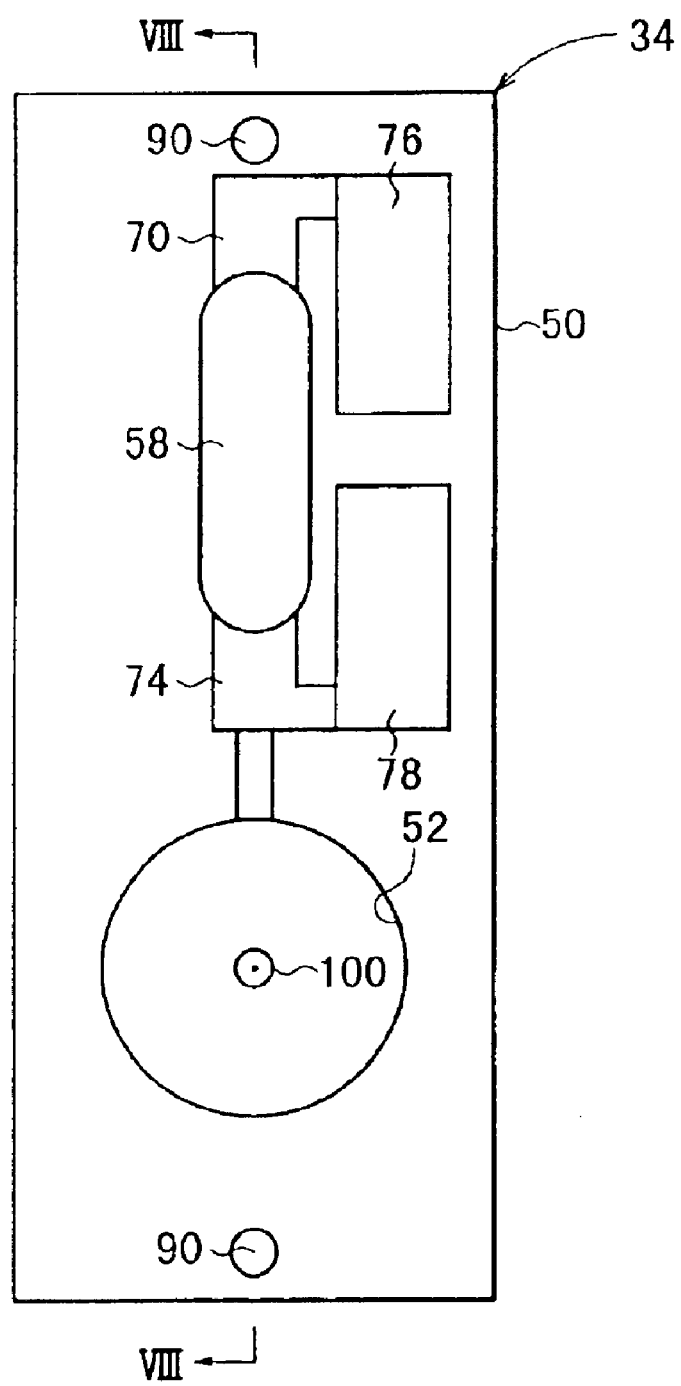
FIG. 7 shows a plan view illustrating an arrangement of a micropipette according to a first modified embodiment.
Figure 8:
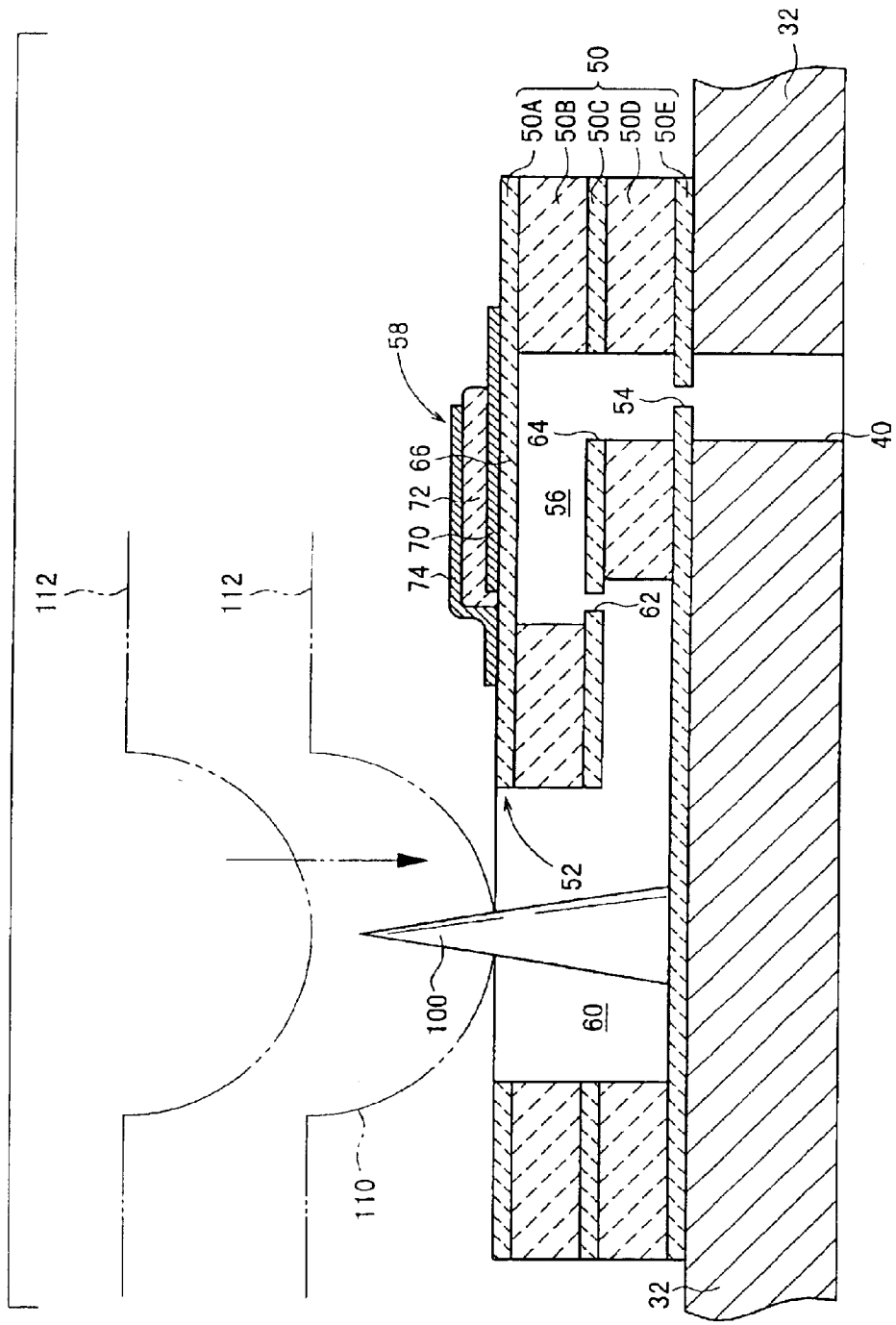
FIG. 8 shows a sectional view taken along a line VII—VII shown in FIG. 7.
Figure 9:
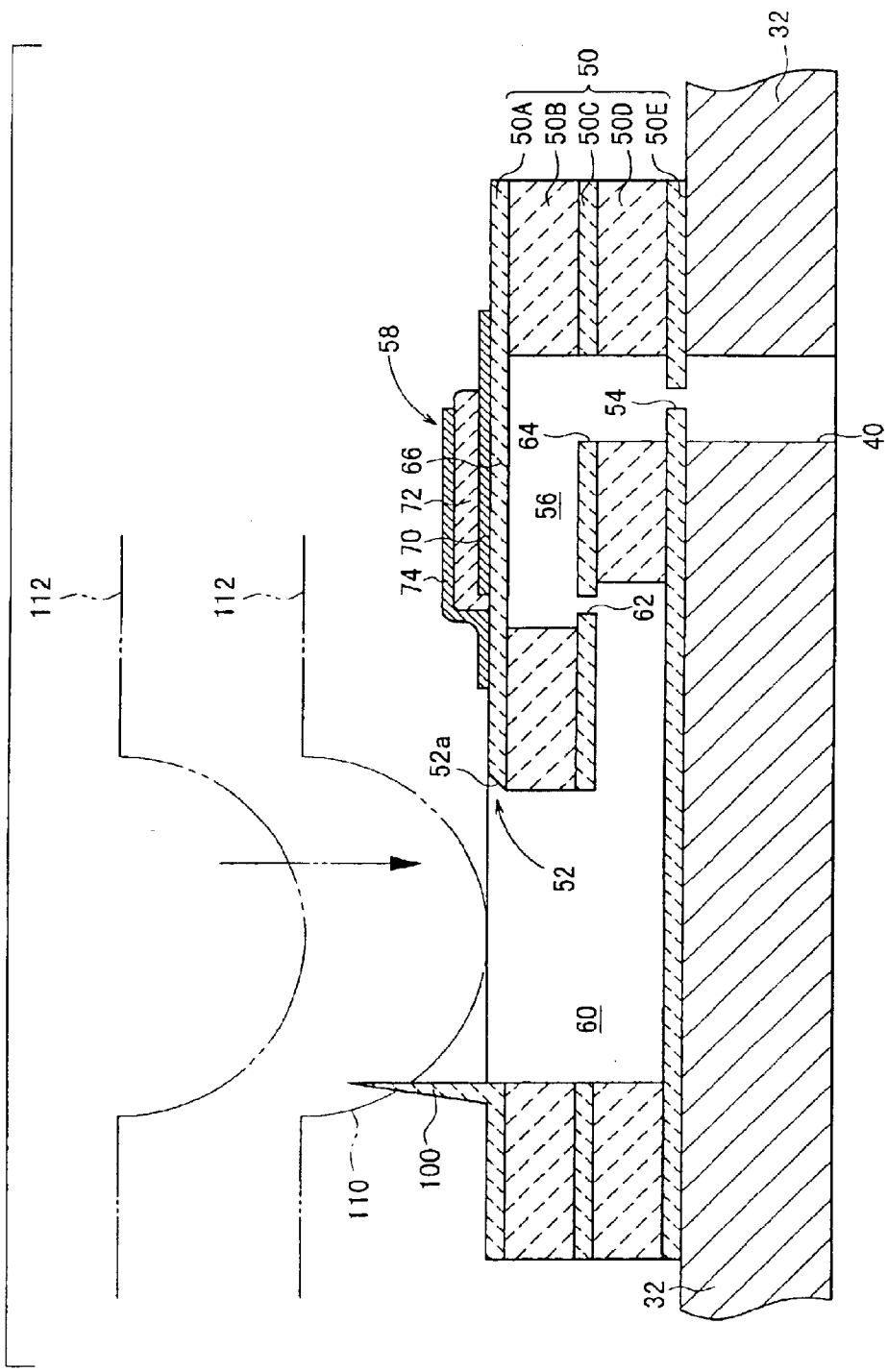
FIG. 9 shows a sectional view illustrating an arrangement of a micropipette according to a second modified embodiment.

Other arrangements are available, including, for example, an arrangement in which the pin 100 is bonded to the bottom of the introducing bore 60 communicating with the sample-pouring port 52 (first modified embodiment), for example, as shown in FIGS. 7 and 8, and an arrangement in which the circumferential edge 52a of the sample-pouring port 52 is chamfered, and the pin 100 is bonded to a part f the circumferential edge 52a (second modified embodiment) as shown in FIG. 9. The pin 100 may be formed, for example, by the aid of the adhesive. Alternatively, the pin 100 may be formed by means of integrated sintering of zirconia ceramics.

The dispenser 30A is constructed such that the plurality of micropipettes 34 each having the sample-pouring port 52 and the sample discharge port 54 are provided in an upstanding manner with the respective sample discharge ports 54 directed downwardly.

That is, the respective micropipettes 34 are arranged such that the respective sample-pouring ports 52 are disposed on the upper side, the sample discharge ports 54 are disposed on the lower side, and the respective sample discharge ports 54 are aligned two-dimensionally. Sample solutions of mutually different types are discharged from the sample discharge ports 54 respectively.

When the dispenser 30A constructed as described above is used, several methods are available to supply the sample solutions of mutually different types corresponding to the respective sample-pouring ports 52. That is, as shown in FIG. 1, for example, a method is available which is based on the use of a cartridge 112 arranged with a large number of recesses (storage sections) 110 each having a substantially V-shaped cross section.

Specifically, explanation will be made with reference to FIGS. 1, 3, 8, 9, and 10 to 12 for several methods for pouring the sample solution to the respective micropipettes 34 of the dispenser 30A by using the cartridge 112.

In the first method, at first, mutually different types of sample solutions are charged in the respective storage sections 110 of the cartridge 112. After that, as shown in FIG. 1, the cartridge 112 is positioned over the dispenser 30A with the forward ends (apexes) of the storage sections 110 directed downwardly.

Subsequently, the cartridge 112 is moved toward the dispenser 30A. As shown in FIGS. 3, 8, and 9, the apex of the storage section 110 contacts with the pin 100 provided on each of the micropipettes 34 at the stage at which the spacing distance between the cartridge 112 and the dispenser 30A is a predetermined distance. When the cartridge 112 is further moved downwardly, the apex of the storage section 110 is pierced by the pin 100. As a result, a hole is bored through each of the storage sections 110.

When the cartridge 112 is slightly moved upwardly at the stage at which the hole is bored through the storage section 110, the sample solution leaks from the gap between the hole and the pin 100. The leaked sample solution is transmitted through the pin 100, and it is introduced into the sample-pouring port 52. The sample solution passes through the introducing bore 60 and the first communication hole 62, and it is introduced into the cavity 56.

In the first method, it is preferable that the gas is fed under pressure from the position over the cartridge toward the cartridge 112 at least when the hole is bored through the apex of the storage section 110. Accordingly, it is possible to shorten the period of time required to perform the pouring process.

Figure 10:
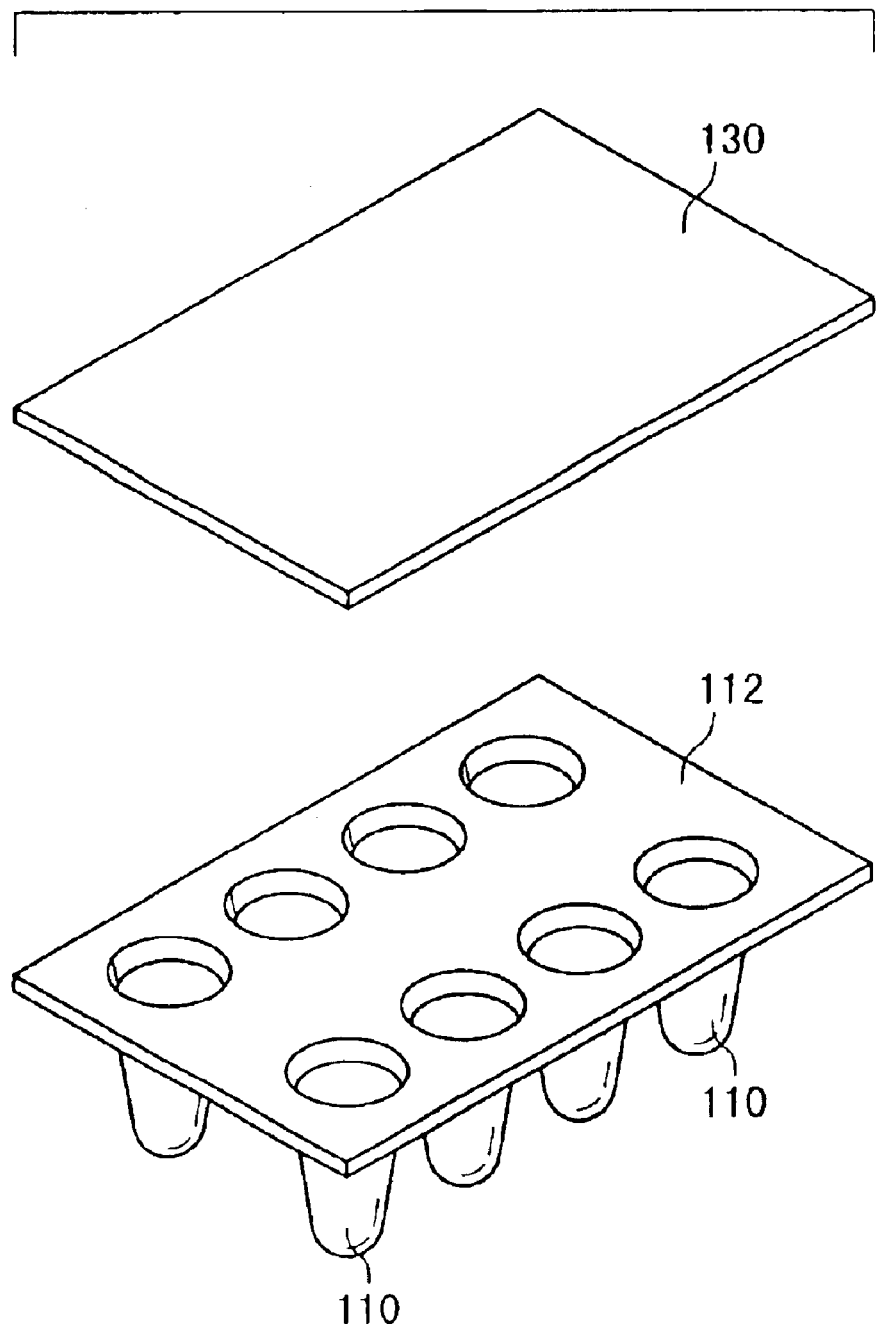
FIG. 10 illustrates a second method for producing a DNA chip by using the dispenser, depicting a state in which a film member is stuck to close respective storage sections of the cartridge.
Figure 11:
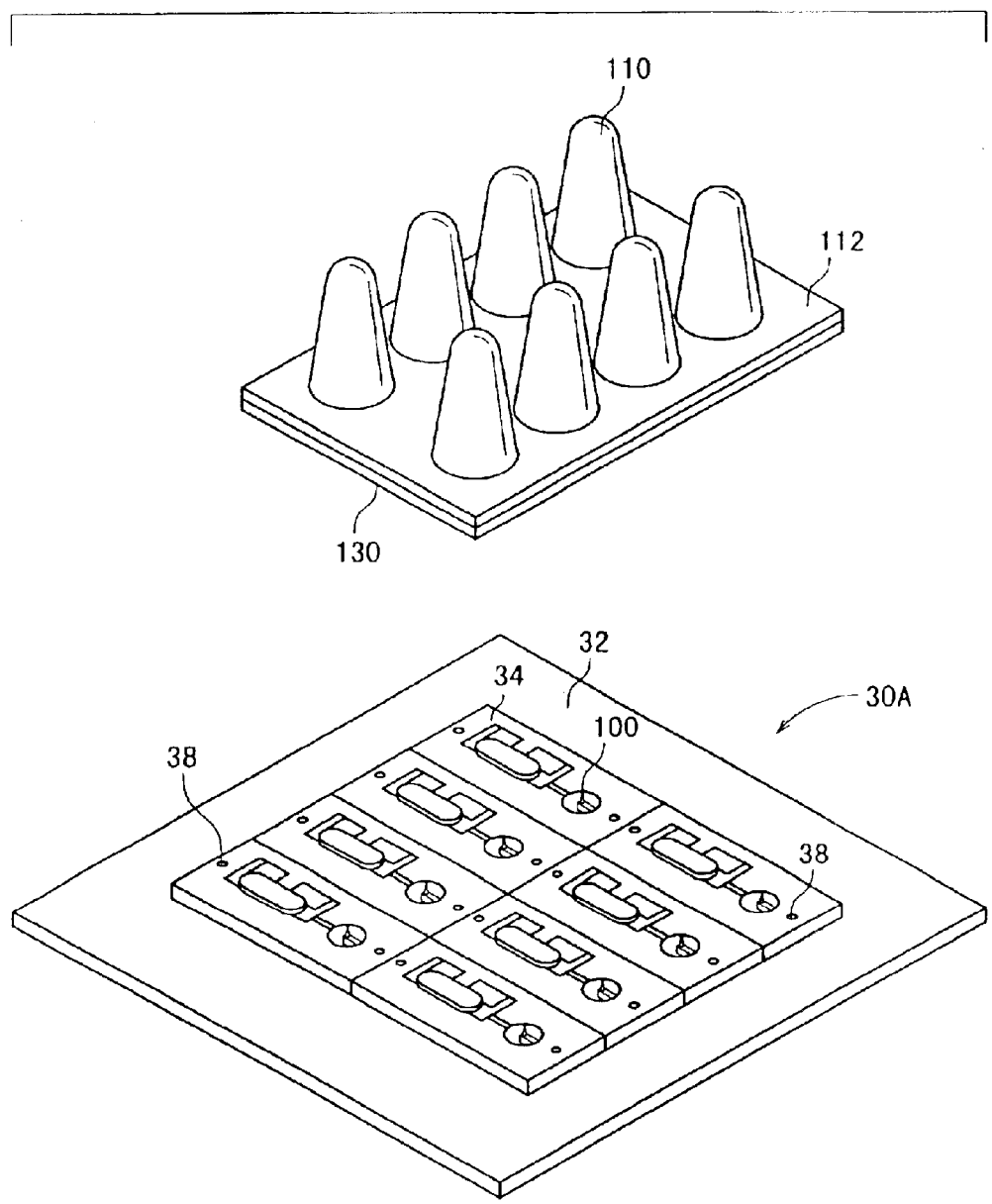
FIG. 11 illustrates a state in which the cartridge stuck with the film member is transported to a position over the dispenser.

Next, in the second method, at first, mutually different types of sample solutions are charged in the respective storage sections 110 of the cartridge 112. After that, as shown in FIG. 10, a thin film member 130 is stuck to close the respective storage sections 110 of the cartridge 112. Subsequently, as shown in FIG. 11, the cartridge 112 is positioned over the dispenser 30A with the forward ends (apexes) of the storage sections 110 directed upwardly. That is, the film member 130 is opposed to the dispenser 30A.

Figure 12:
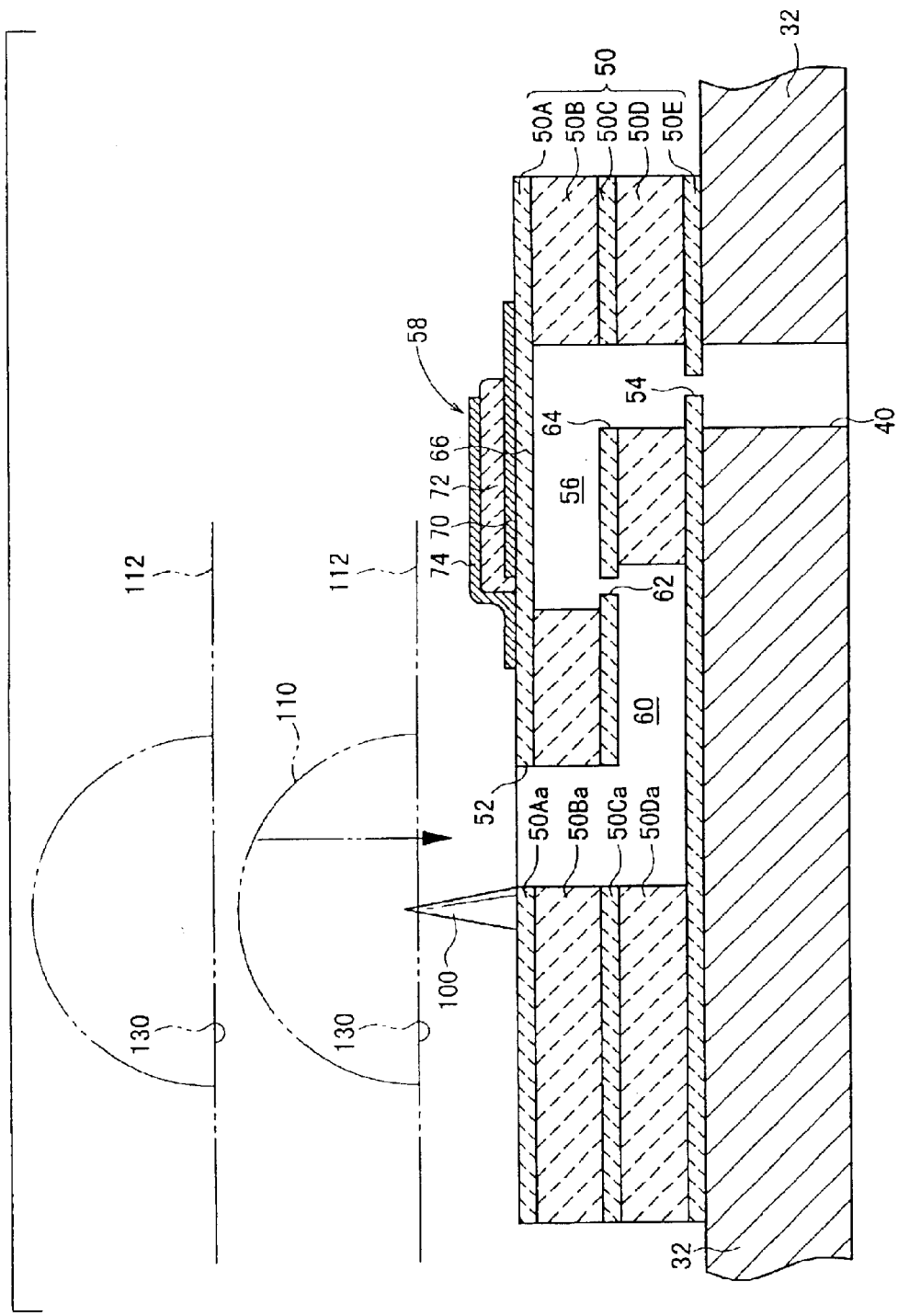
FIG. 12 shows a sectional view illustrating a state in which a hole is bored through the film member with the micropipette.

Subsequently, the cartridge 112 is moved toward the dispenser 30A. As shown in FIG. 12, the film member 130 contacts with the pin 100 provided on each of the micropipettes 34 at the stage at which the spacing distance between the cartridge 112 and the dispenser 30A is a predetermined distance. When the cartridge 112 is further moved downwardly, the film member 130 is pierced by the pin 100. As a result, holes are bored through portions of the film member 130 corresponding to the respective storage sections 110.

When the cartridge 112 is slightly moved upwardly at the stage at which the holes are bored through the film member 130, the sample solution leaks from the gap between the hole and the pin 100. The leaked sample solution is transmitted through the pin 100, and it is introduced into the sample-pouring port 52. The sample solution passes through the introducing bore 60 and the first communication hole 62, and it is introduced into the cavity 56.

In the second method, it is preferable that the cartridge 112 is heated at least when the hole is bored through the storage section 110. Accordingly, the sample solution and the gas in each of the storage sections 110 are expanded. Therefore, the sample solution is quickly introduced into the sample-pouring port 52 through the hole bored through the film member 130. As a result, it is possible to shorten the period of time required to perform the pouring process.

As described above, according to the dispenser 30A concerning the first embodiment and the foregoing first and second methods, it is possible to supply the sample solution to each of the micropipettes 34 quickly, efficiently, and reliably. It is possible to perform the steps from the supply of the sample solution to the supply onto the base plate 10. It is possible to improve the quality of the DNA chip 20 and improve the yield.

The first and second methods described above are illustrative of the case of the application to the dispenser 30A having the micropipette 34 in which the pin 100 is secured to the protruding section 50Aa provided for the sample-pouring port 52 as shown in FIGS. 3 and 12. Alternatively, the foregoing procedures are also applicable in an equivalent manner to the dispenser 30A having the micropipette 34 in which the pin 100 is provided on the bottom of the introducing bore 60 as shown in FIG. 8, and the dispenser 30A having the micropipette 34 in which the pin 100 is provided at the circumferential edge 52a of the sample-pouring port 52.

In the first and second methods, it is also preferable to provide a mechanism for washing the space ranging from the sample-pouring port 52 to the sample discharge port 54 formed in the substrate 50 of each of the micropipettes 34. In this arrangement, for example, several thousands to several tens of thousands of types or many kinds of DNA fragments are discharged as the minute spots 80 with good purity without involving any contamination, which is preferred.

As described above, the substrate 50 for constructing the micropipette 34 is formed of ceramics, for which it is possible to use, for example, fully stabilized zirconia, partially stabilized zirconia, alumina, magnesia, and silicon nitride.

Among them, the fully stabilized/partially stabilized zirconia is used most preferably, because the mechanical strength is large even in the case of the thin plate, the toughness is high, and the reactivity with the piezoelectric layer 72 and the electrode material is small.

When the fully stabilized/partially stabilized zirconia is used as the material, for example, for the substrate 50, it is preferable that the portion (vibrating section 66), on which the actuator section 58 is formed, contains an additive such as alumina and titania.

Those usable as the piezoelectric ceramic for the piezoelectric layer 72 for constructing the actuator section 58 include, for example, lead zirconate, lead titanate, lead magnesium niobate, lead magnesium tantalate, lead nickel niobate, lead zinc niobate, lead manganese niobate, lead antimony stannate, lead manganese tungstate, lead cobalt niobate, and barium titanate, and composite ceramics containing components obtained by combining any of them. However, in the first embodiment, a material containing a major component composed of lead zirconate, lead titanate, and lead magnesium niobate is preferably used, because of the following reason.

That is, such a material has a high electromechanical coupling constant and a high piezoelectric constant. Additionally, such a material has small reactivity with the substrate material during the sintering of the piezoelectric layer 72, making it possible to stably form the product having a predetermined composition.

Further, in the first embodiment, it is also preferable to use ceramics obtained by appropriately adding, to the piezoelectric ceramics described above, for example, oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and stannum, or a combination of any of them, or other compounds.

For example, it is also preferable to use ceramics containing a major component composed of lead zirconate, lead titanate, and lead magnesium niobate, and further containing lanthanum and strontium.

On the other hand, it is preferable that the upper electrode 74 and the lower electrode 70 of the actuator section 58 are made of metal which is solid at room temperature and which is conductive. For example, it is possible to use metal simple substance of, for example, aluminum, titanium, chromium, iron, cobalt, nickel, copper, zinc, niobium, molybdenum, ruthenium, palladium, rhodium, silver, stannum, tantalum, tungsten, iridium, platinum, gold, and lead, or alloy obtained by combining any of them. It is also preferable to use a cermet material obtained by dispersing, in the metal described above, the same material as that of the piezoelectric layer 72 or the substrate 50.

The respective actuator sections 58 are driven after the mutually different types of sample solutions are charged to the respective micropipettes 34 in accordance with the first method or the second method described above so that the sample solutions are discharged from the sample discharge ports 54 of the respective micropipettes 34.

As for the electrical signal to be applied to each of the electrodes 70, 74 of the actuator section 58, when the actuator section 58 performs the ON operation to decrease, the volume of the cavity 58, the pulse-shaped voltage is applied to each of the electrodes 70, 74. In this procedure, for example, the displacement amount and the displacement speed of the vibrating section 66 are changed by changing, for example, the amplitude (voltage) of the pulse, the amount of change per unit time (rising angle of the voltage waveform), and the pulse width. Accordingly, it is possible to control the discharge amount of the sample solution. The number of dripping operations for the sample solution per unit time can be altered by changing the number of pulses to be generated during a certain period.

Figure 13A:
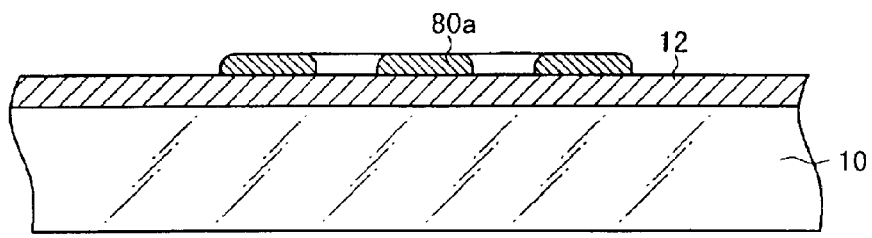
FIG. 13A shows a sectional view illustrating the process in which a sample solution is supplied onto a base plate, and a large number of minute spots are formed within one spot to be formed.
Figure 13B:
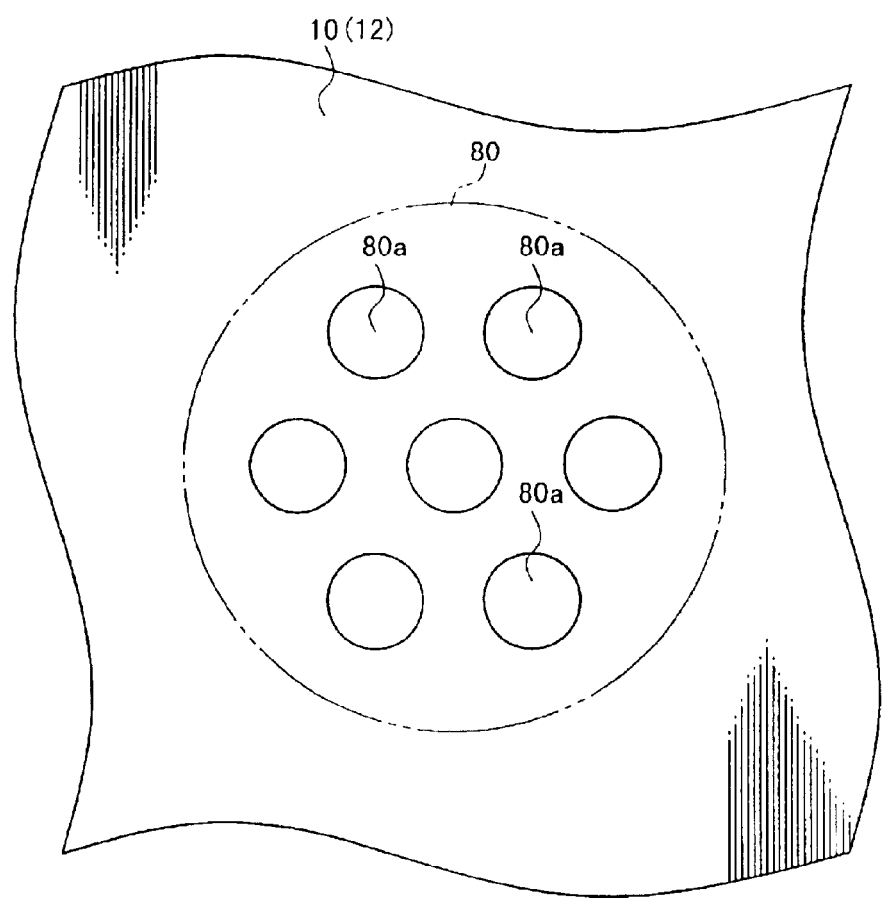
FIG. 13B shows a plan view thereof.
Figure 14A:
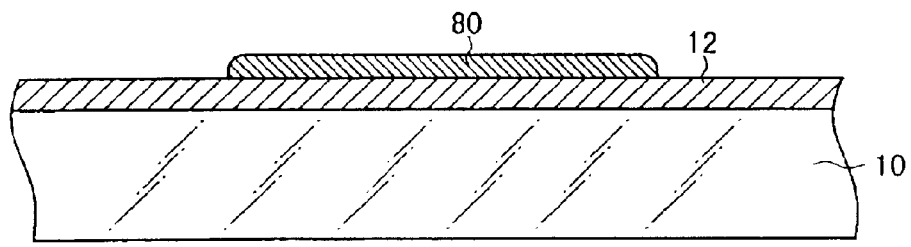
FIG. 14A shows a sectional view illustrating a state in which the large number of minute spots are combined to form one spot on the base plate.
Figure 14B:
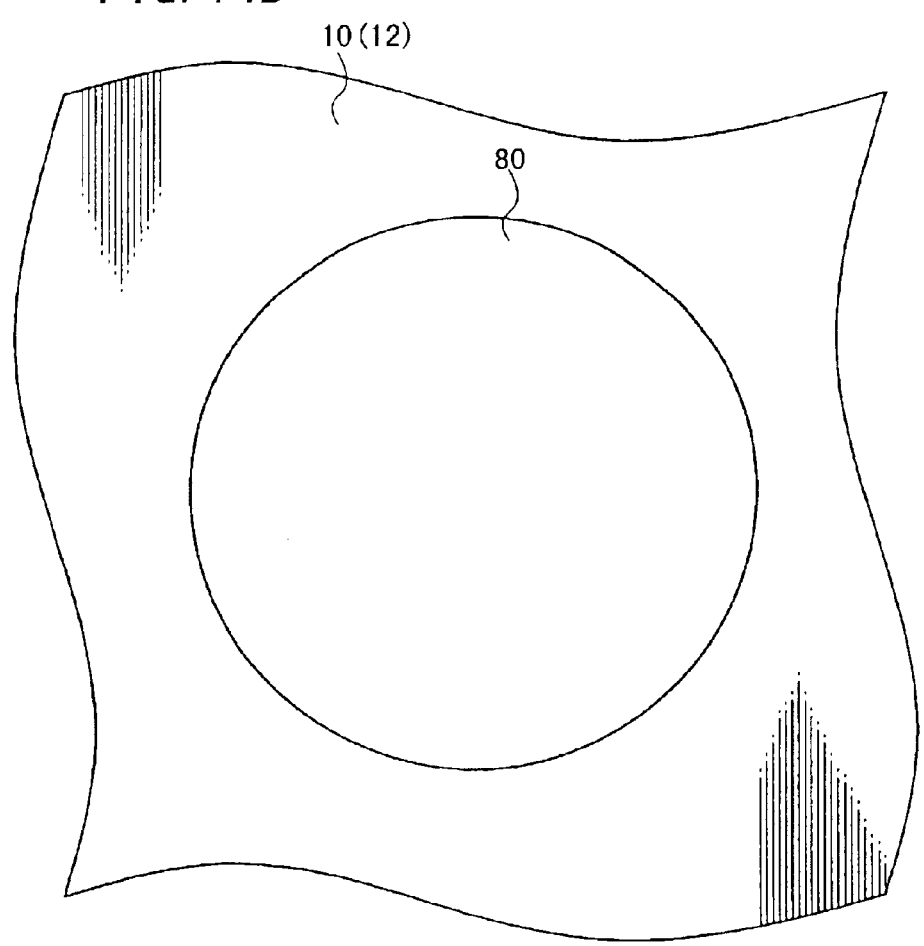
FIG. 14B shows a plan view thereof.

When one spot 80 is formed by supply a plurality of drops of the sample solution, the number of supply times is usually increased while fixing the supply position. However, the supply position may be deviated every time when the supply is performed. For example, as shown in FIGS. 13A and 13B, minute spots 80a based on a plurality of drops of the sample solution are formed within one spot 80 (indicated by a two-dot chain line) to be formed, by appropriately changing the supply position of the sample solution. The minute spots 80a are combined (integrated) on the base plate 10. Accordingly, as shown in FIGS. 14A and 14B, one spot 80 is formed. In this process, it is possible to obtain a uniform diameter of the respective spots 80 formed on the base plate 10, by controlling the number of supply times, the supply position, and the supply amount for one time of operation, depending on the type of the sample solution to be supplied.

It is preferable that a voltage of such a degree to excite the vibration is applied to the actuator section 58 after the sample solution is charged into the cavity 56. Accordingly, the DNA fragments contained in the sample solution charged in the cavity are fully dispersed, and thus no dispersion occurs in the amount of the DNA fragments for every supply operation.

In the embodiments described above, the pins 100 are provided for the respective micropipettes 34 of the dispenser 30A. Alternatively, as shown in FIG. 15, a pin 100 may be externally used to bore a hole through each of the storage sections 110 of the cartridge 112 (third method) without providing the pin 100 for each of the micropipettes 34.

Figure 15:
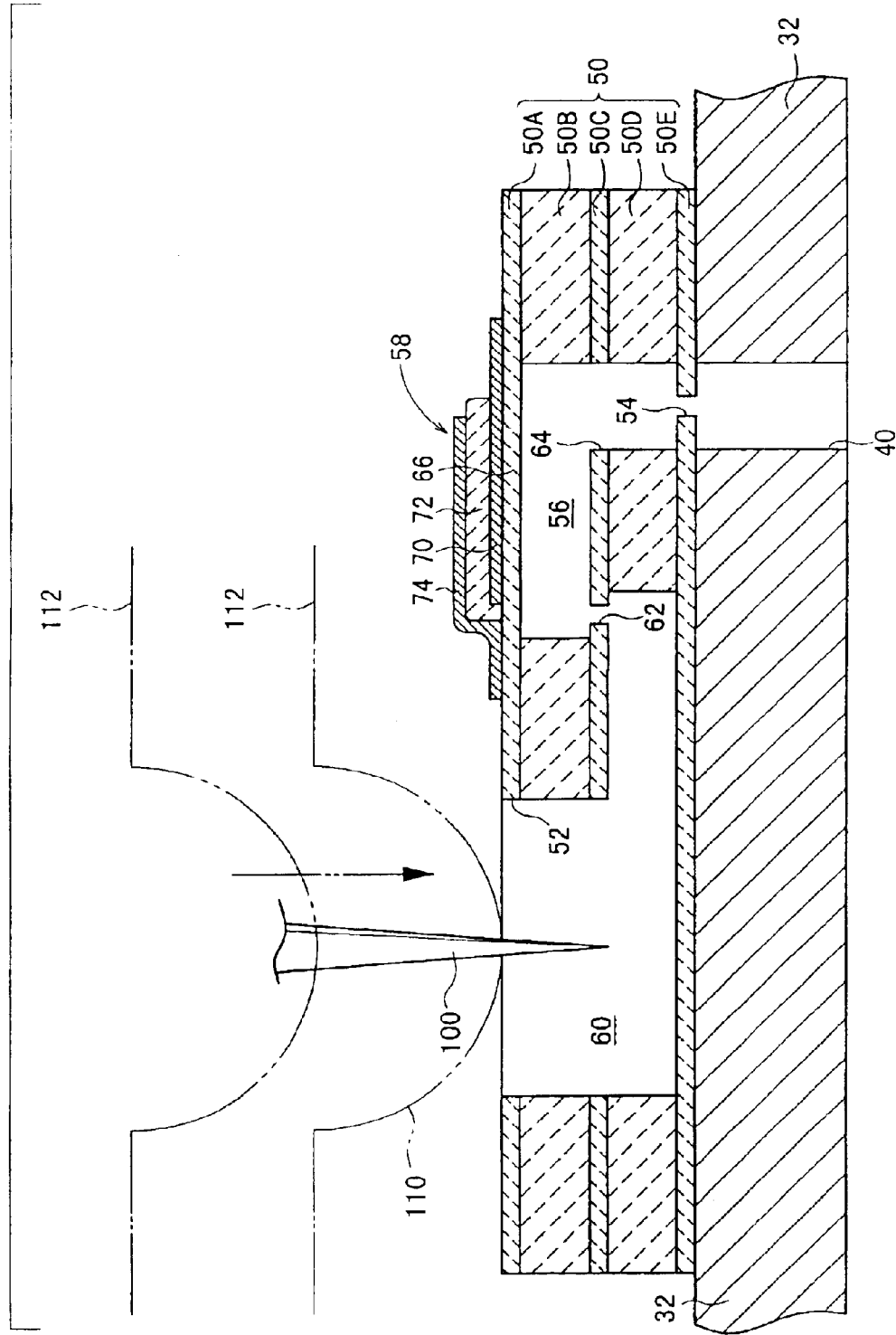
FIG. 15 illustrates a third method for producing a DNA chip by using the dispenser.

That is, as shown in FIG. 15, the dispenser 30A to be used is provided with no pin 100 at the sample-pouring port 52 of each of the micropipettes 34. As shown by two-dot chain lines, the storage section 110 is pierced by the pin 100 from the position over each of the storage sections 110, for example, at the stage at which each of the storage sections 110 of the cartridge 112 contacts with the sample-pouring port 52 of the micropipette 34 or the former is disposed closely to the latter to bore a hole through the storage section 110.

When the pin 100 is pulled out at the stage at which the hole is bored through the storage section 110, then the sample solution is discharged from the hole, and it is introduced into the sample-pouring port 52. The sample solution passes through the introducing bore 60 and the first communication hole 62, and it is introduced into the cavity 56.

The dispenser 30A according to the first embodiment described above is illustrative of the case in which the arrangement pitch of the respective micropipettes 34 is approximately the same as the arrangement pitch of the respective storage sections 110 of the cartridge 112. Alternatively, as in a dispenser 30B according to a second embodiment shown in FIGS. 16A and 16B, it is also preferable that the arrangement pitch of the respective micropipettes 34 is variable.

Figure 16A:
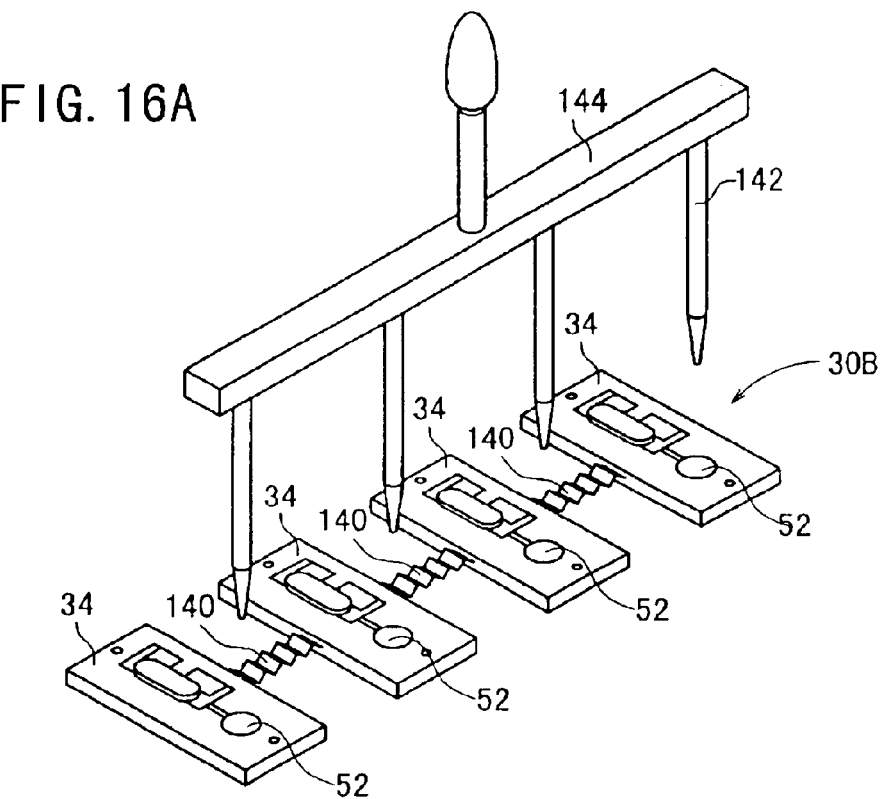
FIG. 16A illustrates a state in which a sample solution is supplied from a solution supply apparatus to the dispenser according to the second embodiment.
Figure 16B:
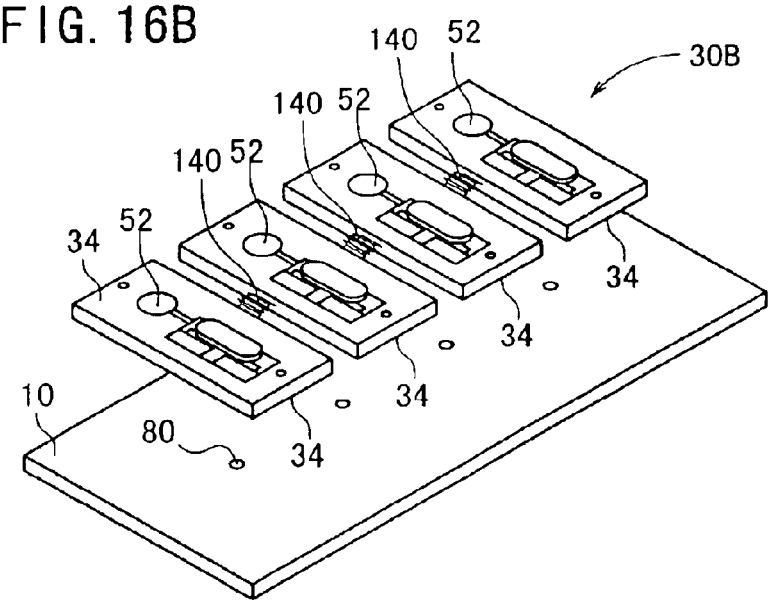
FIG. 16B illustrates a state in which the sample solution is supplied from the dispenser according to the second embodiment onto a base plate.

That is, as shown in FIGS. 16A and 16B, the dispenser 30B according to the second embodiment is provided with a pitch-varying mechanism 140 for varying the arrangement pitch of the respective micropipettes 34. Those adoptable as the pitch-varying mechanism 140 include, for example, a mechanism based on a screw, a mechanism based on a spring, and a mechanism based on a combination of the foregoing mechanisms.

Especially, when the dispenser 30B according to the second embodiment is used, as shown in FIG. 16A, it is possible to use a solution supply apparatus 144 comprising a large number of arranged pipettes 142.

The variation of the arrangement pitch of the respective micropipettes 34 is set as follows. That is, for example, when the arrangement pitch of the respective micropipettes 34 is minimum with the pitch-varying mechanism 140, as shown in FIG. 16B, the pitch is optimum for the supply onto the base plate 10. For example, when the arrangement pitch is maximum, as shown in FIG. 16A, the arrangement pitch is approximately the same as the arrangement pitch of the respective pipettes 142 of the solution supply apparatus 144. The foregoing setting is preferably adopted because it is possible to suppress the dispersion concerning the pitch between the respective micropipettes 34.

When the dispenser 30B is used, at first, as shown in FIG. 16A, the arrangement pitch of the respective micropipettes 34 is maximized by using the pitch-varying mechanism 140 to give approximately the same arrangement pitch as the arrangement pitch of the respective pipettes 142 of the solution supply apparatus 144. In this state, the sample solution is supplied from the solution supply apparatus 144 to the respective micropipettes 34 of the dispenser 30B.

At the stage at which the supply of the sample solution to the dispenser 30B is completed, as shown in FIG. 16B, the pitch-varying mechanism 140 is used to minimize the arrangement pitch of the respective micropipettes 34. Subsequently, the dispenser 30B is transported to the position over the base plate 10, and then the actuator sections 58 of the respective micropipettes 34 are driven. The sample solution is discharged and supplied onto the base plate 10 to form the minute spots 80 on the base plate 10.

Concerning the dispenser 30B according to the second embodiment and the production method based on the use of the dispenser 306, it is possible to perform the supply of the sample solution from the solution supply apparatus 144 to the dispenser 30B and the supply of the sample solution from the dispenser 30B onto the base plate 10 quickly, efficiently, and reliably. It is possible to smoothly perform the steps from the supply of the sample solution to the supply onto the base plate 10. It is possible to improve the quality of the DNA chip 20 and improve the yield.

Figure 17A:
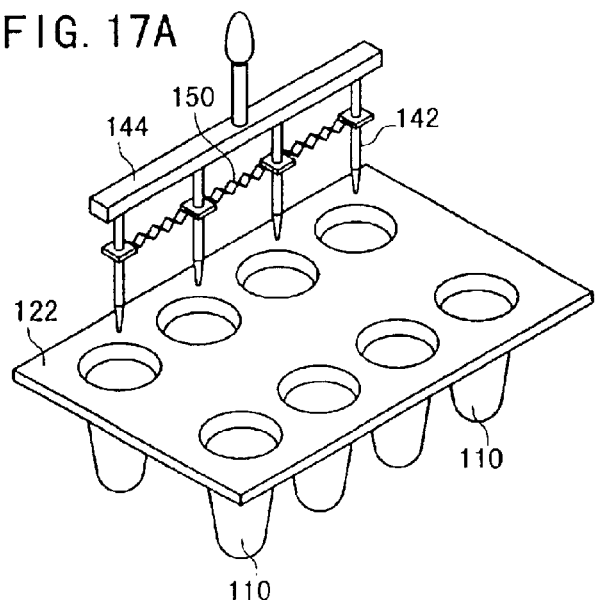
FIG. 17A illustrates a state in which the sample solution is supplied from the respective storage sections of the cartridge to the solution supply apparatus.
Figure 17B:
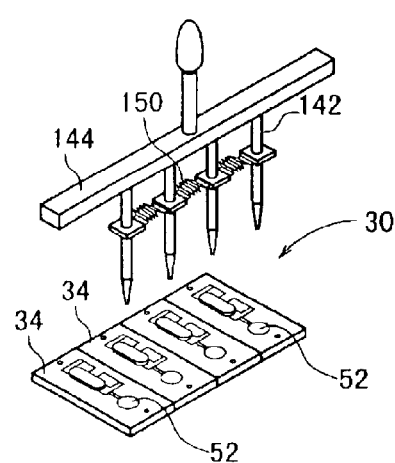
FIG. 17B illustrates a state in which the sample solution is supplied from the solution supply apparatus to the dispenser.

In the second embodiment described above, the pitch-varying mechanism 140 is provided for the dispenser 30B. Alternatively, as shown in FIGS. 17A and 17B, a pitch-varying mechanism 150 may be provided for the solution supply apparatus 144. The pitch-varying mechanism 150 has a mechanism for varying the arrangement pitch of the respective pipettes 142 for constructing the solution supply apparatus 144. Those adoptable as the pitch-varying mechanism 150 include, for example, a mechanism based on a screw, a mechanism based on a spring, and a mechanism based on a combination of the foregoing mechanisms.

In this case, as shown in FIG. 17B, it is possible to use a dispenser 30 in which the arrangement pitch of the respective micropipettes is fixed to be a pitch optimum to supply the sample solution onto the base plate 10.

The variation of the arrangement pitch of the respective pipettes 142 of the solution supply apparatus 144 is set as follows. That is, for example, when the arrangement pitch of the respective pipettes 142 is minimum with the pitch-varying mechanism 150, as shown in FIG. 17B, the pitch is the arrangement pitch of the sample-pouring ports 52 of the respective micropipettes 34 of the dispenser 30. For example, when the arrangement pitch of the respective pipettes 142 is maximum, as shown in FIG. 17A, the arrangement pitch is approximately the same as the arrangement pitch of the respective storage sections 110 of the cartridge 112. The foregoing setting is preferably adopted because it is possible to suppress the dispersion concerning the pitch between the respective pipettes 142 of the solution supply apparatus 144.

When the solution supply apparatus 144 is used, at first, as shown in FIG. 17A, the arrangement pitch of the respective pipettes 142 is maximized by using the pitch-varying mechanism 150 to give approximately the same pitch as the arrangement pitch of the respective storage sections 110 of the cartridge 112. In this state, the sample solution, which is stored in the storage section 110 of the cartridge 112, is sucked and introduced into the solution supply apparatus 144 by the aid of each of the pipettes 142.

At the stage at which the supply of the sample solution to the solution supply apparatus 144 is completed, as shown in FIG. 17B, the arrangement pitch of the respective pipettes 142 is minimized by using the pitch-varying mechanism 150 to give approximately the same pitch as the arrangement pitch of the respective micropipettes 34 of the dispenser 30. In this state, the sample solution is supplied from the solution supply apparatus 144 to each of the micropipettes 34 of the dispenser 30.

Figure 17C:
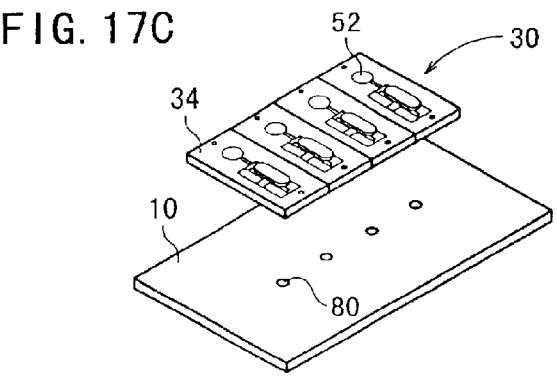
FIG. 17C illustrates a state in which the sample solution is supplied from the dispenser onto the base plate.

At the stage at which the supply of the sample solution to the dispenser 30 is completed, as shown in FIG. 17C, the dispenser 30 is transported to the position over the base plate 10. After that, the actuator sections 58 of the respective micropipettes 34 are driven to discharge and supply the sample solution onto the base plate 10. Thus, the minute spots 80 are formed on the base plate 10.

As described above, in the production method based on the use of the solution supply apparatus 144 having the pitch-varying mechanism 150, it is possible to perform the supply of the sample solution from the cartridge 112 to the solution supply apparatus 144, the supply of the sample solution from the solution supply apparatus 144 to the dispenser 30, and the supply of the sample solution from the dispenser 30 onto the base plate 10 quickly, efficiently, and reliably. It is possible to smoothly perform the steps from the supply of the sample solution to the supply onto the base plate 10. It is possible to improve the quality of the DNA chip 20 and improve the yield.

Next, a dispenser 30C according to a third embodiment will be explained with reference to FIGS. 18 to 22.

Figure 18:
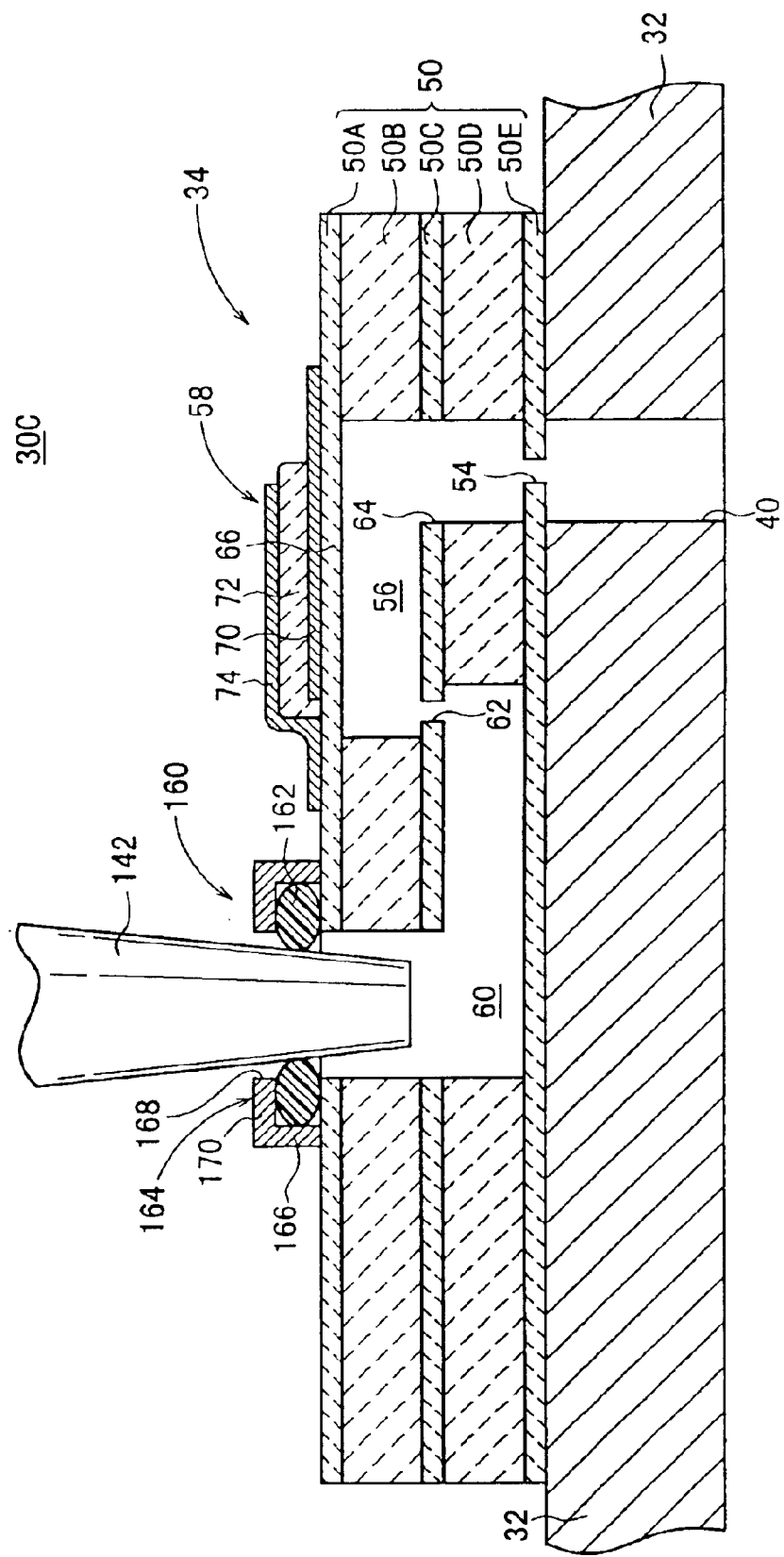
FIG. 18 shows a sectional view illustrating an arrangement of a micropipette of a dispenser according to a third embodiment.

As shown in FIG. 18, the dispenser 30C according to the third embodiment is especially applicable to the dispenser 30B according to the second embodiment and the dispenser 30 shown in FIG. 17B. The dispenser 30C comprises a holding fit section 160 for holding each of the pipettes 142 of the solution supply apparatus 144, the holding section 160 being formed at a circumferential edge of the sample-pouring port 52 of each of the micropipettes 34. The holding section 160 includes, for example, an O-ring which is provided at the circumferential edge of the sample-pouring port 52, and a fixation section 164 for fixing the O-ring 162.

Figure 19:
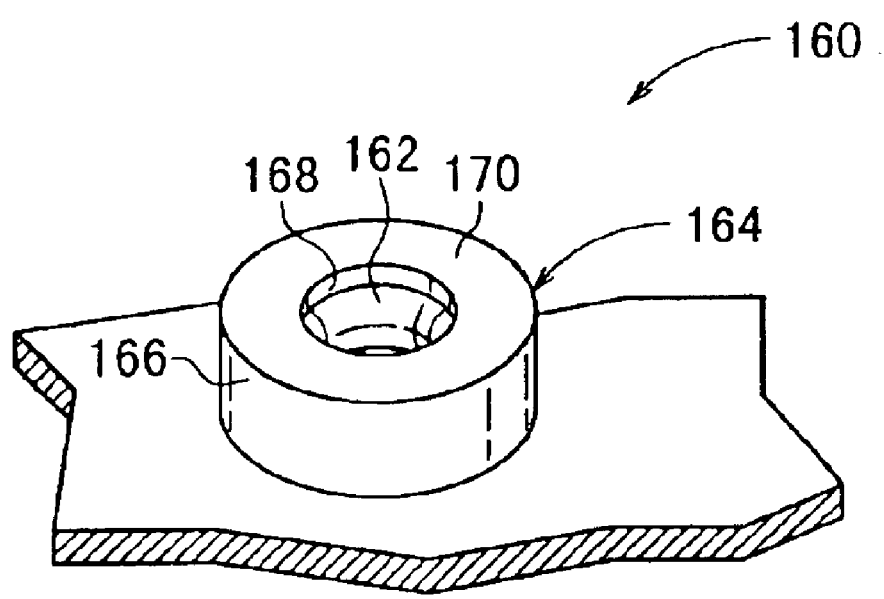
FIG. 19 shows a perspective view illustrating an example of a holding section.

As shown in FIG. 19, for example, the fixation section 164 is integrally formed with a side wall 166 which is formed to have a ring-shaped configuration, and an upper wall 170 which is formed with a circular hole 168 for preventing upward disengagement of the O-ring 162. The fixation section 164 may be formed integrally with the substrate 50. Alternatively, the fixation section 164 may be formed as a member separate from the substrate 50, and it may be secured onto the substrate 50, for example, by the aid of an adhesive. FIG. 18 is illustrative of the case in which the fixation section 164 is secured with an adhesive.

Figure 20:
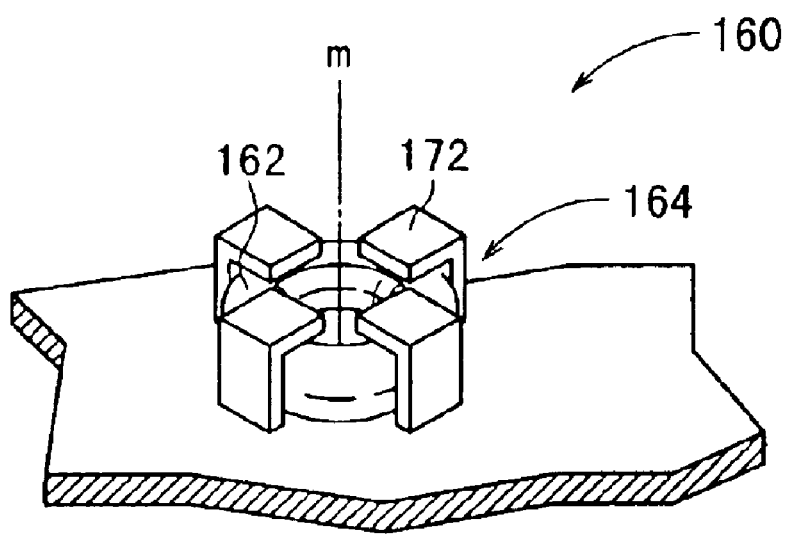
FIG. 20 shows a perspective view illustrating another example of the holding section.

Another example of the fixation section 164 is shown, for example, in FIG. 20. That is, the fixation section 164 is constructed by providing a plurality of (four in the example shown in FIG. 20) L-shaped holding tabs 172 with their upper portions bent toward the axis m of the sample-pouring port 52.

When the sample solution is used for each of the micropipettes 34 of the dispenser 30C according to the third embodiment by using the solution supply apparatus 144, as shown in FIG. 18, the forward end of each of the pipettes 142 of the solution supply apparatus 144 is inserted into the O-ring 162 of the holding section 160 of each of the corresponding micropipettes 34.

Figure 21:
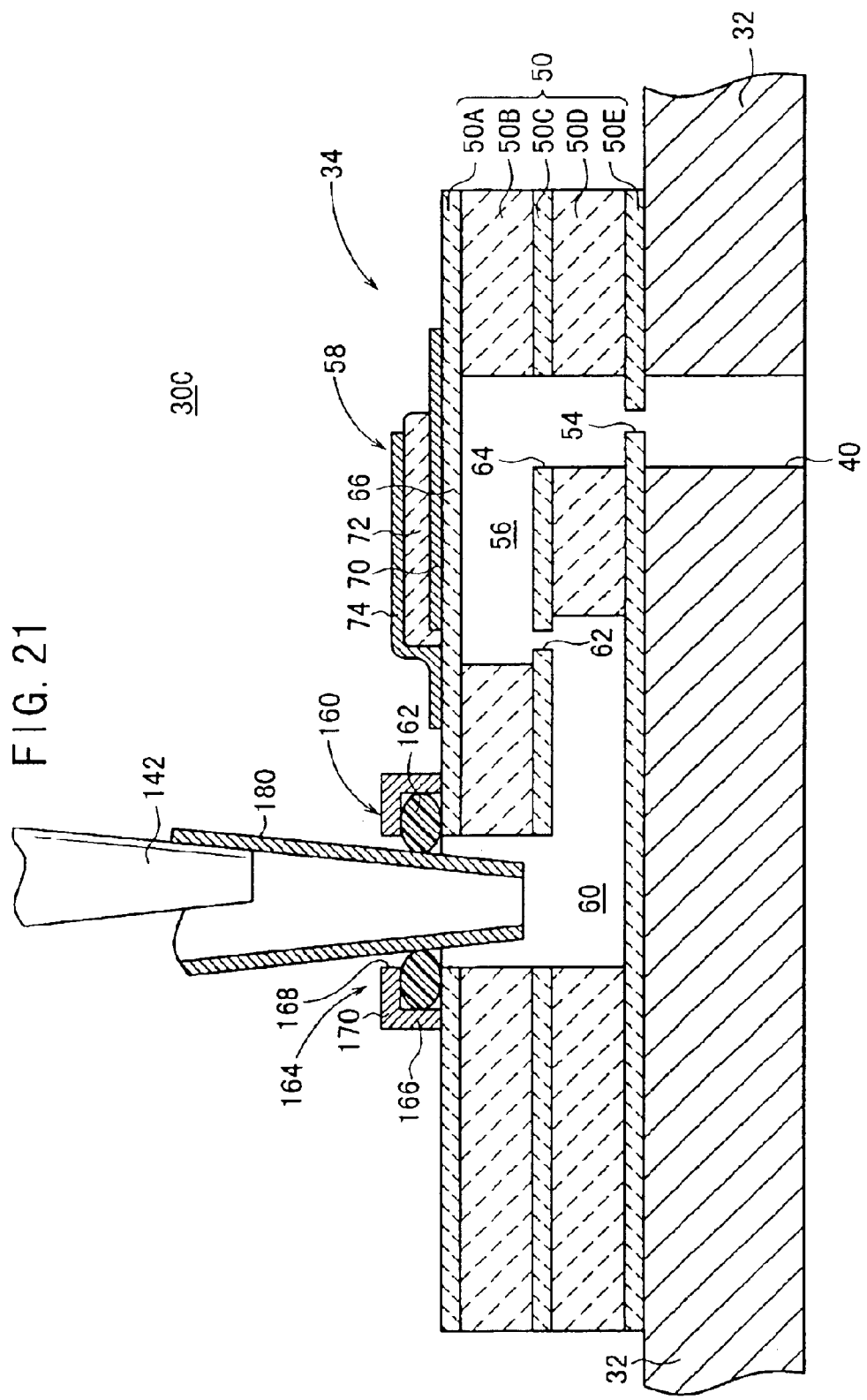
FIG. 21 shows a sectional view illustrating an arrangement of another example of the micropipette of the dispenser according to the third embodiment.

Another example of the supply of the sample solution is shown, for example, in FIG. 21. In this case, a tube 180, into which each of the pipettes 142 of the solution supply apparatus 144 is insertable, is held by the holding section 160 to supply the sample solution to the micropipette 34. It is possible to use the tube 180 in which the diameter is set to be gradually increased upwardly, and the diameter of the lower end is set to be approximately the same as the inner diameter of the O-ring 162.

When the tube 180 as described above is used, the operation is preferably performed while allowing the forward end of the pipette 142 to approach the inner wall of the tube 180, because of the following reason. That is, when the operation is performed as described above, no inconvenience arises, which would be otherwise caused, for example, such that the sample solution discharged from the pipette 142 collides with the inner wall of the tube 180, and it is scattered.

In the case of the dispenser 30C according to the third embodiment, when the sample solution is poured into each of the micropipettes 34 of the dispenser 30C by using the pipette 142, the pipette 142 or the tube 180 is held by the holding section 160. Therefore, the sample solution can be reliably poured into the micropipette 34. It is possible to effectively avoid any solution leakage or the like.

Especially, when at least the inner wall of the tube 180 is subjected to a hydrophilic treatment, the sample solution discharged from the pipette 142 can be reliably introduced into the sample-pouring port 52 of the micropipette 34, which is preferred.

Still another example of the supply of the sample solution is shown, for example, in FIG. 22. That is, a scale 182 for measuring the amount of liquid poured into the tube 180 is formed at a part of the tube 180 for receiving each of the pipettes 142 of the solution supply apparatus 144. Further, a portion provided with a projection 184 for making contact with a part of each of the pipettes 142, and a portion provided with no projection 184 may be formed at positions of an identical distance from the sample-pouring port 52 on a part of the inner wall of the tube 180.

In FIG. 22, a filter 186, which is formed with a large number of openings having an opening area of not more than an opening area of the sample discharge port 54, is attached between the tube 180 and the sample-pouring port 52 by holding the circumference with the holding section 160, the substrate 50, and an adhesive 188, in order to remove any foreign matter in the sample solution to be poured.

In this arrangement, the holding section 160 is composed of an elastic member such as a rubber as a whole. The tube 180 is held in an air-tight manner by only the holding section. The amount of the poured sample solution can be confirmed while pouring the sample solution by the aid of the scale 182. When the pouring is performed while allowing the projection 184 to make contact with each of the pipettes 142, then the pouring position is always constant, and it is possible to reduce the dispersion of the pouring operation. Further, the portion, at which the projection 184 is not formed, constitutes a path for allowing the gas to escape during the pouring. Therefore, the pouring operation can be performed in a reliable manner without involving any bubble in the sample solution.

Further, the filter 186 can be used to shut off any contamination of foreign matter into the micropipette 34 and avoid any discharge failure which would be otherwise caused by clogging of foreign matter. It is preferable that the size (diameter) of the opening portion of the filter 186 is not more than the size (diameter) of the discharge port. However, if the opening is too small, it is difficult to pour the sample solution. Therefore, it is more preferable that the size (diameter) of the opening portion of the filter 186 is about 70% of the opening diameter of the discharge port.

As described above, when the DNA chip 20 is produced by using any one of the dispensers 30A to 30C according to the first to third embodiments and the solution supply apparatus 144 shown in FIG. 17A, it is possible to smoothly perform the steps from the supply of the sample solution to the supply onto the base plate 10. It is possible to improve the quality of the DNA chip 20 and improve the yield.

Especially, when each of the sample-pouring ports 52 is subjected to the hydrophilic treatment for the dispensers 30A to 30C according to the first to third embodiments and the dispenser 30 shown in FIG. 17B, the sample solution, which is supplied via the sample-pouring port 52, can be smoothly introduced toward the cavity 56. Therefore, it is possible to shorten the period of time required to supply the sample solution.

It is a matter of course that the dispenser and the method for producing the DNA chip according to the present invention are not limited to the embodiments described above, which may be embodied in other various forms without deviating from the gist or the essential characteristics of the present invention.

What is claimed is:

1. A dispenser comprising a plurality of arranged micropipettes each including a pouring port for pouring a sample solution from the outside, a cavity in communication with said pouring port for pouring and charging said sample solution thereinto, and a discharge port in communication with said cavity for discharging said sample solution, each of said micropipettes formed from at least one substrate, and including a piezoelectric/electrostrictive element disposed on at least one wall surface of said at least one substrate which forms said cavity so that said sample solution is movable in said cavity, and said sample solution being discharged from said discharge port of each of said micropipettes, wherein:

a holding section for holding a pipette for pouring said solution into said pouting port is provided at a circumferential edge of said pouring port of each of said micropipettes, each said holding section being separately attached on an outer portion of said substrate at or proximate a circumferential edge of a respective one of said pouring ports.

2. A dispenser comprising a plurality of arranged micropipettes each including a pouring port into which a sample solution from the outside is provided, a cavity in communication with said pouring port, into which said sample solution is supplied, and a discharge port in communication with said cavity from which said sample solution is discharged, each of said micropipettes are formed from at least one substrate, and include a piezoelectric/electrostrictive element disposed on at least one wall surface of said at least one substrate which forms said cavity so that said sample solution is movable in said cavity, wherein:

a holding section for holding a pipette, from which said solution is supplied into said pouring port, is provided at a circumferential edge of said pouring port of each of said micropipettes, and includes a tube for receiving said pipette, each said holding section being separately attached on an outer portion of said substrate at or proximate a circumferential edge of a respective one of said pouring ports.

3. A dispenser comprising a plurality of arranged micropipettes each including a pouring port for pouring a sample solution from the outside, a cavity in communication with said pouring port for pouring and charging said sample solution thereinto, and a discharge port in communication with said cavity for discharging said sample solution, each of said micropipettes formed from at least one substrate, and including a piezoelectric/electrostrictive element disposed on at least one wall surface of said at least one substrate which forms said cavity so that said sample solution is movable in said cavity, and said sample solution being discharged from said discharge port of each of said micropipettes, wherein:

a holding section for holding a pipette for pouring said solution into said pouring port is provided at a circumferential edge of said pouring port of each of said micropipettes, a portion of said holding section being elastic and each said holding section being separately attached on an outer portion of said substrate at or proximate a circumferential edge of a respective one of said pouring ports.

4. A dispenser comprising a plurality of arranged micropipettes each including a pouring port into which a sample solution from the outside is provided, a cavity in communication with said pouring port, into which said sample solution is supplied, and a discharge port in communication with said cavity from which said sample solution is discharged, each of said micropipettes are formed from at least one substrate, and include a piezoelectric/electrostrictive element disposed on at least one wall surface of said at least one substrate which forms said cavity so that said sample solution is movable in said cavity, wherein:

a holding section for holding a pipette, from which said solution is supplied into said pouring port, is provided at a circumferential edge of said pouring port of each of said micropipettes, and includes a tube for receiving said pipette, a portion of said holding section being elastic and each said holding section being separately attached on an outer portion of said substrate at or proximate a circumferential edge of a respective one of said pouring ports.

5. The dispenser according to claim 2, wherein at least the inner wall of said tube for receiving said pipette is subjected to a hydrophilic treatment.

6. The dispenser according to claim 2, further comprising a scale for measuring an amount of liquid poured into said tube formed at least on a part of said tube for receiving said pipette.

7. The dispenser according to claim 2, further comprising a plurality of projections formed on a part of the inner wall of said tube for receiving said pipette, said projections being spaced apart and positioned on said inner wall substantially the same axial distance from said pouring port.

8. The dispenser according to claim 2, further comprising a filter attached to portions of said at least one substrate and said holding section between said pouring port and said tube for receiving said pipette, said filter having a large number of openings defining an opening area on the surface of the filter, and said opening area having a surface area that is not larger than an opening area of said discharge port.

9. The dispenser according to claim 1, wherein said pouring port is subjected to a hydrophilic treatment.

* * * * *

UNITED STATES PATENT AND TRADEMARK OFFICE
CERTIFICATE OF CORRECTION

PATENT NO. : 6,814,937 B1
DATED : November 9, 2004
INVENTOR(S) : Toshikazu Hirota et al.

It is certified that error appears in the above-identified patent and that said Letters Patent is hereby corrected as shown below:

Column 2,
Line 30, change "makes" to -- make --

Column 4,
Line 1, after "reliably." add -- The pin may be provided on the bottom of the pouring port so that the sample solution can be introduced into the pouring port even more reliably. --

Column 18,
Line 12, change "pouting" to -- pouring --

Signed and Sealed this

Eighth Day of February, 2005

JON W. DUDAS
*Director of the United States Patent and Trademark Office*